US008901246B2

(12) United States Patent
McManus et al.

(10) Patent No.: US 8,901,246 B2
(45) Date of Patent: Dec. 2, 2014

(54) METHOD FOR PREPARING BRANCHED FUNCTIONALIZED POLYMERS USING BRANCHED POLYOL CORES

(71) Applicant: Nektar Therapeutics, San Francisco, CA (US)

(72) Inventors: Samuel P. McManus, Guntersville, AL (US); Antoni Kozlowski, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 14/051,246

(22) Filed: Oct. 10, 2013

(65) Prior Publication Data
US 2014/0039205 A1  Feb. 6, 2014

Related U.S. Application Data

(62) Division of application No. 11/459,268, filed on Jul. 18, 2006, now Pat. No. 8,568,705.

(60) Provisional application No. 60/700,114, filed on Jul. 18, 2005.

(51) Int. Cl.
| A61K 31/00 | (2006.01) |
| C08G 65/48 | (2006.01) |
| A61K 31/74 | (2006.01) |
| C08G 71/04 | (2006.01) |
| C08G 65/329 | (2006.01) |
| A61K 47/48 | (2006.01) |
| C08G 65/34 | (2006.01) |
| C07D 405/14 | (2006.01) |
| A61K 31/765 | (2006.01) |

(52) U.S. Cl.
CPC .......... *A61K 47/48061* (2013.01); *C08G 65/48* (2013.01); *A61K 31/74* (2013.01); *C08L 2203/02* (2013.01); *C08G 71/04* (2013.01); *C08G 65/329* (2013.01); *A61K 47/48215* (2013.01); *C08G 65/34* (2013.01); *C07D 405/14* (2013.01); *A61K 31/765* (2013.01)
USPC ........................................................ 525/56

(58) Field of Classification Search
USPC .............. 424/78.08, 78.37; 525/56, 123, 410; 549/370
See application file for complete search history.

(56) References Cited

U.S. PATENT DOCUMENTS

| 3,101,374 A | 8/1963 | Patton, Jr. |
| 4,278,555 A | 7/1981 | Zaweski et al. |
| 4,670,417 A | 6/1987 | Iwasaki et al. |
| 4,894,238 A | 1/1990 | Embry et al. |
| 5,122,614 A | 6/1992 | Zalipsky |
| 5,135,751 A | 8/1992 | Henry et al. |
| 5,252,710 A | 10/1993 | Dazey et al. |
| 5,252,714 A | 10/1993 | Harris et al. |
| 5,281,698 A | 1/1994 | Nitecki |
| 5,306,501 A | 4/1994 | Viegas et al. |
| 5,429,826 A | 7/1995 | Nair et al. |
| 5,468,478 A | 11/1995 | Saifer et al. |
| 5,543,158 A | 8/1996 | Gref et al. |
| 5,605,976 A | 2/1997 | Martinez et al. |
| 5,610,241 A | 3/1997 | Lee et al. |
| 5,618,528 A | 4/1997 | Cooper et al. |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,681,567 A | 10/1997 | Martinez et al. |
| 5,681,576 A | 10/1997 | Henry |
| 5,681,811 A | 10/1997 | Ekwuribe |
| 5,684,096 A | 11/1997 | Taylor et al. |
| 5,756,593 A | 5/1998 | Martinez et al. |
| 5,824,784 A | 10/1998 | Kinstler et al. |
| 5,874,500 A | 2/1999 | Rhee et al. |
| 5,900,461 A | 5/1999 | Harris |
| 5,919,455 A | 7/1999 | Greenwald et al. |
| 5,932,462 A | 8/1999 | Harris et al. |

(Continued)

FOREIGN PATENT DOCUMENTS

| EP | 0 462 408 | 5/1991 |
| EP | 0 473 268 | 3/1992 |

(Continued)

OTHER PUBLICATIONS

Notification of Transmittal of the International Search Report and the Written Opinion of the International Searching Authority, or the Declaration, mailed Dec. 4, 2006, corresponding to PCT Application No. PCT/US2006/027529.

(Continued)

*Primary Examiner* — Gregory Listovoyb
(74) *Attorney, Agent, or Firm* — Mark A. Wilson

(57) ABSTRACT

A method of preparing a multiarm polymer includes reacting a branched polyol with one or more functionalizing reagents to effect substitution of an ionizable functional group or a protected ionizable functional group, Y, to form a mixture comprising (i) unsubstituted branched polyol containing no Y groups; (ii) a monosubstituted polyol comprising one Y group, and (iii) a multisubstituted polyol (e.g., a disubstituted polyol comprising two Y groups); followed by purifying the mixture to separate the monosubstituted polyol from other species Thereafter, a water-soluble and non-peptidic polymer segment is attached to the monosubstituted branched polyol at the site of at least one of the hydroxyl groups. The invention also provides purified monosubstituted branched polyols and multiarm polymers prepared by the method and polyol precursors for use in the method.

6 Claims, 3 Drawing Sheets

(56) References Cited

U.S. PATENT DOCUMENTS

| | | | |
|---|---|---|---|
| 5,965,566 | A | 10/1999 | Greenwald et al. |
| 6,011,042 | A | 1/2000 | Greenwald et al. |
| 6,051,648 | A | 4/2000 | Rhee et al. |
| 6,096,331 | A | 8/2000 | Desai et al. |
| 6,113,906 | A | 9/2000 | Greenwald et al. |
| 6,166,130 | A | 12/2000 | Rhee et al. |
| 6,210,717 | B1 | 4/2001 | Choi et al. |
| 6,258,351 | B1 | 7/2001 | Harris |
| 6,323,278 | B2 | 11/2001 | Rhee et al. |
| 6,348,558 | B1 | 2/2002 | Harris et al. |
| 6,362,254 | B2 | 3/2002 | Harris et al. |
| 6,362,276 | B1 | 3/2002 | Harris et al. |
| 6,376,604 | B2 | 4/2002 | Kozlowski |
| 6,436,425 | B1 | 8/2002 | Henry et al. |
| 6,448,369 | B1 | 9/2002 | Bentley et al. |
| 6,455,369 | B1 | 9/2002 | Yasukohehi et al. |
| 6,497,895 | B2 | 12/2002 | Uhrich |
| 6,515,100 | B2 | 2/2003 | Harris |
| 6,602,498 | B2 | 8/2003 | Shen |
| 6,624,246 | B2 | 9/2003 | Kozlowski |
| 6,730,334 | B2 | 5/2004 | Zhao |
| 6,815,530 | B2 | 11/2004 | Ekwuribe et al. |
| 6,835,802 | B2 | 12/2004 | Ekwuribe et al. |
| 7,026,440 | B2 | 4/2006 | Bentley et al. |
| 8,568,705 | B2 | 10/2013 | McManus et al. |
| 2002/0013408 | A1 | 1/2002 | Rhee et al. |
| 2002/0052443 | A1 | 5/2002 | Greenwald et al. |
| 2005/0009988 | A1* | 1/2005 | Harris et al. ............ 525/56 |
| 2005/0036978 | A1 | 2/2005 | Kozlowski |
| 2005/0054816 | A1 | 3/2005 | McManus et al. |
| 2006/0116534 | A1 | 6/2006 | Samuelsson et al. |
| 2011/0256225 | A1* | 10/2011 | Ghoroghchian et al. ..... 424/489 |

FOREIGN PATENT DOCUMENTS

| | | |
|---|---|---|
| EP | 0 614 666 | 9/1994 |
| EP | 0 899 310 | 3/1999 |
| EP | 1 283 233 | 2/2003 |
| JP | 08165343 | 6/1996 |
| JP | 3067541 | 7/2000 |
| WO | WO 92/00748 | 1/1992 |
| WO | WO 94/26778 | 11/1994 |
| WO | WO 96/03984 | 2/1996 |
| WO | WO 99/29303 | 6/1999 |
| WO | WO 99/45964 | 9/1999 |
| WO | WO 00/65024 | 11/2000 |
| WO | WO 01/49268 | 7/2001 |
| WO | WO 02/060978 | 8/2002 |
| WO | WO 03/047549 | 6/2003 |
| WO | WO 03/094850 | 11/2003 |
| WO | WO 2004/060965 | 7/2004 |
| WO | WO 2004/060966 | 7/2004 |
| WO | WO 2004/083153 | 9/2004 |
| WO | WO 2005/010075 | 2/2005 |
| WO | WO 03/094850 | * 11/2005 |

OTHER PUBLICATIONS

Notification Concerning Transmittal of International Preliminary Report on Patentability and Written Opinion of the International Searching Authority, dated Jan. 22, 2008.

Examination Report mailed Oct. 1, 2009, corresponding to European Application No. 06 800 077.7-2115.

Examination Report mailed Jun. 18, 2010, corresponding to European Application No. 06 800 077.7-2115.

Extended European Search Report mailed Apr. 16, 2012, corresponding to European Application No. 11180764.0-2115.

Enzon Pharmaceuticals, Macromolecular Engineering Technologies, 16 pages, (2004).

Nektar™—Transforming Therapeutics, Nektar Molecule Engineering: Polyethylene Glycol and Derivatives for Advanced PEGylation, 24 pages, Catalog—2003, (Jul. 2003).

Nektar™—Transforming Therapeutics, Nektar Advanced PEGylation: Polyethylene Glycol and Derivatives for Advanced PEGylation, 27 pages, Catalog—2004, (Jul. 2004).

NOF Corporation, PEG Derivatives, Phospholipid and Drug Delivery Materials for Pharmaceuticals, 46 pages, Catalogue 2003-$1^{st}$, (Jan. 2003).

NOF Corporation, PEG Derivatives, Phospholipid and Drug Delivery Materials for Pharmaceuticals, 27 pages, Catalogue 2003-$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

Konopikova, et al., "Synthesis and Fungicidal Activity of Isoxazolines Fused to 3,5-Dichloromaleimide", Collect. Czech. Chem. Commun., vol. 57, pp. 1521-1536, (1992).

European Communication corresponding to European Patent Application No. 11 180 764.0 dated May 3, 2013.

Nektar™—Transforming Therapeutics, Nektar Advanced PEGylation: Polyethylene Glycol and Derivatives for Advanced PEGylation, 33 pages, (Catalog 2005-2006).

* cited by examiner

METHOD FOR PREPARING BRANCHED FUNCTIONALIZED POLYMERS USING BRANCHED POLYOL CORES

CROSS REFERENCE TO RELATED APPLICATIONS

This application is a divisional application of U.S. patent application Ser. No. 11/458,269, filed Jul. 18, 2006, now U.S. Pat. No. 8,568,705, which application claims the benefit of priority to provisional application Ser. No. 60/700,114, filed on Jul. 18, 2005, which is incorporated herein by reference

FIELD OF THE INVENTION

Among other things, this invention relates to water-soluble and non-peptidic polymers prepared using branched polyol core molecules, and in particular, to methods for making, purifying, and utilizing such polymers and precursors thereof.

BACKGROUND OF THE INVENTION

Covalent attachment of the hydrophilic polymer, poly(ethylene glycol), abbreviated "PEG," to molecules and surfaces is of considerable utility in areas such as biotechnology and medicine. PEG is a polymer that possesses many beneficial properties. For instance, PEG is soluble in water and in many organic solvents, is non-toxic and non-immunogenic, and when attached to a surface, PEG provides a biocompatible, protective coating. Common applications or uses of PEG include (i) covalent attachment to proteins, e.g., for extending plasma half-life and reducing clearance through the kidney, (ii) attachment to surfaces such as in arterial replacements, blood contacting devices, and biosensors, (iii) as a soluble carrier for biopolymer synthesis, and (iv) as a reagent in the preparation of hydrogels.

In many if not all of the uses noted above, it is necessary to first activate the PEG by converting one or both of its hydroxyl termini, if it is a linear PEG, to a functional group capable of readily reacting with a functional group found within a desired target molecule or surface, such as a functional group found on the surface of a protein. For proteins, typical reactive amino acids include lysine, cysteine, histidine, arginine, aspartic acid, glutamic acid, serine, threonine, tyrosine, the N-terminal amino group and the C-terminal carboxylic acid.

The PEG used as a starting material for most PEG activation reactions is typically an end-capped PEG. An end-capped PEG, in a linear PEG form, is one where one of the hydroxyl groups is converted into a non-reactive group, such as a methoxy, ethoxy, or benzyloxy group. In branched PEG structures having several hydroxyl end groups, one or more of them may be end-capped. Most commonly used is methoxyPEG, abbreviated as mPEG. End-capped PEGs such as mPEG are generally preferred, since such end-capped PEGs are typically more resistant to cross-linking and aggregation. The structures of two commonly employed end-capped PEG alcohols, mPEG and monobenzyl PEG (otherwise known as bPEG), are shown below,

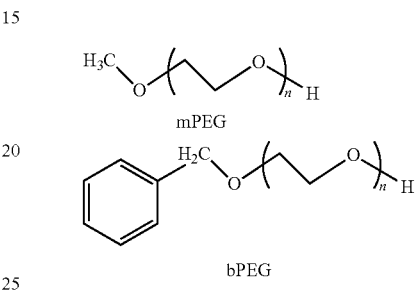

wherein n typically ranges from about 10 to about 2,000.

Despite many successes, conjugation of a polymer to an active agent is often challenging. For example, attaching a relatively long poly(ethylene glycol) molecule to an active agent typically imparts greater water solubility than attaching a shorter poly(ethylene glycol) molecule. However, some conjugates bearing such long poly(ethylene glycol) moieties have been known to be substantially inactive in vivo. It has been hypothesized that these conjugates are inactive due to the length of the poly(ethylene glycol) chain, which effectively "wraps" itself around the entire active agent, thereby blocking access to potential ligands required for activity.

The problem associated with inactive conjugates bearing relatively large poly(ethylene glycol) moieties has been solved, in part, by using "branched" forms of a polymer derivative. Examples of a branched version of a poly(ethylene glycol) derivative are conventionally referred to as "mPEG2-N-hydroxysuccinimide" and "mPEG2-aldehyde" as shown below;

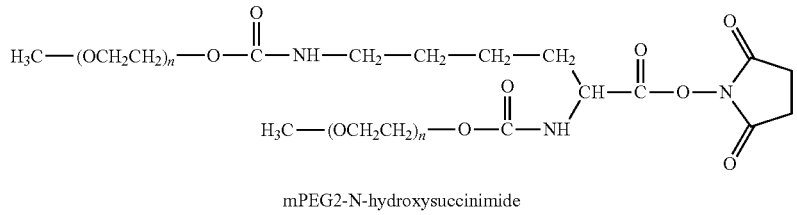

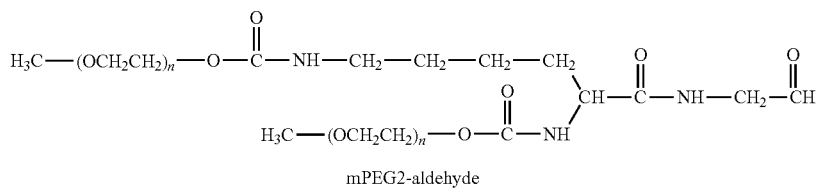

wherein n represents the number of repeating ethylene oxide monomer units. Other branched polymer structures comprise a polyol core, such as a glycerol oligomer, having multiple polymer arms covalently attached thereto at the sites of the hydroxyl groups. Exemplary branched polymer structures having a polyol core are described in U.S. Pat. No. 6,730,334.

Another reason for using branched structures like those above relates to the desire to increase circulation time of the polymer-bound drug. Larger polymers are known to have a longer circulation time than smaller polymers. Hence, drugs attached to the higher molecular weight polymers have longer circulation times, thus reducing the dosing requirements of the drug, which is often injected. There is also a practical aspect in the synthesis of the higher molecular weight polymeric reagents that favors the use of branched structures. As most mPEGs are synthesized by polymerization initiated by a small mPEG fragment, e.g. $CH_3CH_2CH_2O^-Na^+$, any moisture present leads to the formation of PEG diol, a contaminant that leads to a difunctional PEG derivative. At a constant moisture content in the reactor, the amount of diol increases as the molecular weight of the final polymer is increased. Thus while the diol content is rather low with low molecular weight mPEGs, it is quite high with mPEGs with molecular weights around 30,000 Daltons or higher. Because branched PEGs are formed from smaller mPEGs, there is less difunctional influence on the higher molecular weight PEGs formed in this way than in comparable high molecular weight PEGs that are linear. Even in branched PEGs using mPEGs of medium molecular weights (~20,000 Daltons) there are significant enough amounts of impurities introduced by diols to cause concern. Methods to remove these types of impurities typically involve chromatography of acidic or basic intermediates, e.g., see U.S. Pat. No. 5,932,462.

Multiarm polymers are especially attractive for the delivery of small drug molecules. By activating multiple arms at the termini, the overall polymer loading is increased. Thus, on a given multiarm polymer, the effective dose size per gram of polymer is doubled, tripled, quadrupled etc, as two, three, four, etc. arms, respectively, are conjugated with a small drug molecule. Despite the interest in using them for drug delivery, making these multiarm polymers truly useful has presented challenges. For example, the increased structural complexity of branching often results in a concomitant increase in synthetic complexity and/or purification difficulties. In the case of branched polymers based on polyol core molecules, the commercially available ethoxylated polyol cores are typically crude mixtures of oligomers of various molecular weights. For instance, pentaerythritol itself is available in high purity, yet commercially available ethoxylated derivatives are generally crude mixtures having highly variable chain lengths among the various arms. Invariably, there is one pentaeryritol arm that is largely unreacted in these mixtures and, because of the steric hindrance added by the three substituted arms, ultimate conversion of the fourth arm to a useable arm in a predictable manner is very difficult. Purification of these mixtures to give pure versions of a single multiarm, especially to eliminate the fraction having the unusable (unsubstituted) arm, is very difficult because common methods of purification, such as recrystallization, distillation, and chromatography, do not work for these highly viscous liquids or amorphous solids. The crude mixture of multiarm products that result from the use of the commercially available ethoxylated polyols are poorly suited for pharmaceutical applications where large polymer polydispersity values and structural variability are disfavored and high purity levels and a consistent composition must be achieved.

As a result, there is an ongoing need in the art for more readily synthesized and/or purified branched polymer derivatives that can be conveniently used in conjugation reactions with active agents. The present invention addresses this and other needs in the art.

SUMMARY OF THE INVENTION

The present invention provides a method of producing highly pure, branched polymer structures (i.e., multiarm structures) comprising water-soluble and non-peptidic polymer segments or arms extending from a branched polyol core, and branched polyols and multiarm polymers formed using the method. The method of the invention involves attachment of an ionizable functional group to the branched polyol core, either before or after attachment of the polymer segments, which enables purification of the branched polyol core, either before or after polymer attachment, by ion exchange chromatography. In certain embodiments, to avoid functionalizing all hydroxyl groups of the polyol core molecule with the ionizable functional group, a certain number of the hydroxyl groups are in protected form prior to the functionalizing reaction. However, unless all but one of the hydroxyl groups are protected, it is typical for the functionalizing reaction that introduces the ionizable group to result in a plurality of functionalized polyols distinguishable by the number of ionizable groups carried by the polyol.

Thus, in one aspect, the present invention provides a method of preparing a multiarm polymer comprising reacting a branched polyol, in one or more reaction steps, with one or more functionalizing reagents to effect substitution of an ionizable functional group or a protected ionizable functional group, —Y, to form a mixture comprising (i) unsubstituted branched polyol containing no —Y groups; (ii) a monosubstituted polyol comprising a single —Y group, and (iii) a multisubstituted polyol (e.g., a disubstituted polyol comprising two —Y groups). The mixture may further include other multisubstituted species, such as trisubstituted polyols and the like, depending on the number of hydroxyl groups on the polyol starting material. Thereafter, the mixture can be purified using ion exchange chromatography, typically involving passing the mixture through a series of ion exchange columns, in order to separate the monosubstituted polyol from the other species of the mixture. The highly pure monosubstituted polyol can then be manipulated further, such as by attachment of polymer segments followed by coupling to a biologically active agent to form a highly pure branched polymer conjugate.

In one embodiment, the invention provides a method of preparing a multiarm polymer, comprising:

(a) optionally, to a branched polyol molecule bearing at least three hydroxyl groups, attaching a water-soluble and non-peptidic polymer segment to the branched polyol at the site of at least one of the hydroxyl groups, the polymer segment terminating in a functional group, which is optionally protected;

(b) optionally, reacting the branched polyol, in one more reaction steps, with one or more hydroxyl-blocking reagents under conditions sufficient to convert at least one hydroxyl group of the branched polyol to a protected hydroxyl group;

(c) reacting (e.g., via a nucleophilic substitution or a nucleophilic addition reaction) the branched polyol, in one or more reaction steps, with one or more functionalizing reagents to effect substitution of an ionizable functional group or a protected ionizable functional group, —Y, to form a mixture comprising (i) unsubstituted branched polyol containing no —Y groups; (ii) a monosubstituted polyol comprising a single —Y group, and (iii) a multisubstituted polyol (e.g., a disubstituted polyol comprising two —Y groups);

(d) in the instance where —Y is a protected ionizable functional group, deprotecting the ionizable functional group;

(e) purifying the mixture to separate the monosubstituted polyol from the unsubstituted and multisubstituted polyol species;

(f) where step (b) is present, deprotecting the at least one protected hydroxyl group of the branched polyol either before or after said purifying step (e); and (g) if optional step (a) is absent, attaching a water-soluble and non-peptidic polymer segment to the monosubstituted branched polyol at the site of at least one of the hydroxyl groups after said deprotecting step (f) and either before or after said purifying step (e).

In one embodiment, the step of reacting the branched polyol, in one more reaction steps, with one or more hydroxyl-blocking reagents comprises reacting under conditions sufficient to convert enough hydroxyl groups to protected hydroxyl groups such that no more than one-third of the hydroxyl groups remain in unprotected form. The protected hydroxyl groups can be, for example, trityl ether, cyclic acetal or ketal groups. Benzyl, diphenylmethyl, or trityl esters are preferred protected hydroxyl groups.

The polymer attaching steps may comprise ethoxylation of the branched polyol or attachment of a preformed polymer segment via a nucleophilic substitution or a nucleophilic addition reaction. In one embodiment, prior to the attaching step, functional group Y is converted to a hydroxyl group. In another embodiment, prior to the attaching step, the hydroxyl groups of the branched polyol are transformed into a different reactive moiety, such as active ester, active carbonate, ortho ester, acetal, aldehyde, aldehyde hydrate, ketone, ketone hydrate, oxime, alkenyl, acrylate, methacrylate, nitrile, primary or secondary amide, imide, acrylamide, active sulfone, amine, hydrazide, thiol, carboxylic acid, isocyanate, isothiocyanate, maleimide, succinimide, vinylsulfone, dithiopyridine, vinylpyridine, amidate, 2-substituted-1,3-oxazoline, 2-substituted 1,3-(4H)-dihydrooxazines, 2-substituted-1,3-thiazoline, 2-substituted 1,3-(4H)-dihydrothiazines, hydroxylamine, iodoacetamide, orthopyridyl disulfide, epoxide, glyoxal, dione, mesylate, tosylate, or tresylate.

The branched polyol molecule utilized in the present invention may be in the form of a crude mixture of polymeric polyols of various structures and having a variable number of available hydroxyl groups, as well as other alcohol molecules such as non-polymeric starting materials (e.g., glycerol). However, at least one of the polyols in the starting mixture will preferably be a branched polyol having at least three available hydroxyl groups according to the formula R(OH)$_p$, wherein R is a branched hydrocarbon, optionally including one or more ether linkages, and p is at least 3, typically 3 to about 25, and preferably 3 to about 10 (e.g., 3, 4, 5, 6, 7, 8, 9, or 10). The branched polyol molecule preferably comprises a branched hydrocarbon, R, comprising at least one ether linkage and from about 5 to about 100 total carbon and oxygen atoms. Exemplary branched polyol molecules include pentaerythritol, oligomers of pentaerythritol, polymers of pentaerythritol, oligomers of glycerol, polymers of glycerol, sugars, and derivatives of sugars bearing at least three hydroxyl groups, any of which may include poly(alkylene glycol) chains of 1 to about 25 monomer units attached to the terminal hydroxyl groups.

The water-soluble and non-peptidic polymer attached to the branched polyol or monosubstituted polyol is preferably PEG, although other polymers could be used, such as other poly(alkylene glycols), poly(olefinic alcohols), poly(vinylpyrrolidone), poly(hydroxyalkylmethacrylamide), poly(hydroxyalkylmethacrylate), poly(saccharides), poly($\alpha$-hydroxy acids), poly(vinyl alcohol), polyphosphazene, polyoxazoline, poly(N-acryloylmorpholine), and copolymers, terpolymers, and mixtures thereof. The total molecular weight of the water-soluble and non-peptidic polymer attached to the branched polyol is from about 44 Da to about 100,000 Da, more preferably about 1,000 Da to about 80,000 Da, and most preferably about 2,000 to about 40,000 Da.

It is preferable for the reacting step involving attachment of the ionizable functional group, —Y, to be carried out under conditions effective to form no more than about 50 percent of the multisubstituted polyol (e.g., disubstituted polyol), more preferably no more than about 30 percent of the multisubstituted polyol (e.g., disubstituted polyol), most preferably no more than about 18 percent of the multisubstituted polyol (e.g., disubstituted polyol). In some embodiments, the reacting step is carried out under conditions effective to form no more than about 7 percent of the multisubstituted polyol (e.g., disubstituted polyol), and in other embodiments, no more than about 4 percent of the multisubstituted polyol (e.g., disubstituted polyol). This reacting step is also preferably conducted under conditions effective to form a ratio of monosubstituted polyol to multisubstituted polyol that is about 1:1 to about 50:1, more preferably about 2:1 to about 40:1, and most preferably about 4:1 to about 20:1.

Any ionizable functional group could be used as functional group —Y, even relatively weak acidic or basic groups. Exemplary ionizable groups include aldehyde hydrate, ketone hydrate, amine, hydrazine, hydrazide, thiol, carboxylic acid, sulfonic acid, primary amide, secondary amide, amidate, 2-substituted-1,3-oxazoline, 2-substituted 1,3-(4H)-dihydrooxazines, 2-substituted-1,3-thiazoline, 2-substituted 1,3-(4H)-dihydrothiazines, dithiopyridine, vinylpyridine, hydroxylamine, and oxime.

The —Y ionizable functional group can be in a protected form, such as a protected carboxylic acid or protected amine. Where —Y is a protected carboxylic acid, the deprotecting step may comprise hydrolyzing the protected carboxylic acid to thereby form a carboxylic acid. Exemplary protected carboxylic acids include esters (e.g., methyl esters or ortho esters), thiolesters, amides, amidates, thioamidates and hydrazides. Where —Y is a protected amine in the form of a carbonitrile or amide, the deprotecting step may comprise reducing the carbonitrile or amide to thereby form an amine, or certain amides, e.g., a N-acetyl PEG amine may be hydrolyzed to form an amine.

In yet another aspect of the invention, the step of purifying the mixture to separate the monosubstituted polyol from the unsubstituted and multisubstituted polyol species comprises passing the mixture, which can be an aqueous or non-aqueous solution, through a first ion exchange column to provide an eluate, wherein said passing the mixture is carried out under conditions effective to adsorb substantially all of the disubstituted or other multisubstituted polyol onto the first column, passing the eluate through a second ion exchange column under conditions effective to adsorb substantially all of the monosubstituted polyol onto the second column, washing the second column with a water or a solution having low ionic strength to remove unsubstituted polyol, and passing a solution having high ionic strength through the second column to desorb the monosubstituted polyol. In one embodiment, the second ion exchange column is connected in series to one or more additional ion exchange columns. In such an embodiment, the washing step further comprises washing the second and one or more additional ion exchange columns and the passing the eluate step further comprises passing the solution having high ionic strength through the second and one or more additional columns.

In a further aspect, the step of purifying the mixture comprised of (i) unsubstituted branched polyol containing no —Y groups; (ii) a monosubstituted polyol comprising a single —Y group, and (iii) a multisubstituted polyol (e.g., disubstituted polyol comprising two —Y groups), comprises:

(i) passing the mixture through a first ion exchange column to provide an eluate, wherein the passing the mixture step is carried out under conditions effective to adsorb substantially all of said multisubstituted polyol (e.g., disubstituted polyol) onto the first column;

(ii) passing the eluate through a second ion exchange column connected in series to one or more additional ion exchange columns under conditions effective to adsorb a fraction of the monosubstituted polyol onto said second column and onto each of the one or more additional columns;

(iii) washing the second column and one or more additional ion exchange columns with a solution having low ionic strength to remove unsubstituted polyol; and (iv) passing a solution having high ionic strength through the second and one or more additional ion exchange columns to desorb the monosubstituted polyol.

In a still further aspect of the invention, the invention provides branched polyol molecules purified chromatographically according to the above-noted method, the branched polyols comprising at least two hydroxyl groups, optionally in protected form, and at least one ionizable functional group (preferably a single ionizable functional group), the branched polyols having a purity of at least about 83%, more preferably at least about 91%, still more preferably at least 95%, yet still more preferably at least 96%, still more preferably at least 97%, yet still more preferably at least 98%, still more preferably at least 99%, and in some cases about 100% purity. As used herein, purity for a given composition refers to the percentage of polymeric species in the composition having the same branched arrangement and the same number and type of termini (wherein variations in molecular weight within one standard deviation of the average are not considered to affect purity).

The purified branched polyol molecules of the invention can, for example, have the structure Y—R(—OH)$_p$, wherein R is a branched hydrocarbon, optionally including one or more ether linkages, and p is at least 2 (e.g., 3 to about 25, more typically 3 to about 10). The R group can include a poly(alkylene glycol) chain of 1 to about 25 monomer units attached to each terminal hydroxyl group. The purified polyol can be derived from a variety of polyol cores such as pentaerythritol, oligomers of pentaerythritol, polymers of pentaerythritol, oligomers of glycerol, polymers of glycerol, and sugar-derived polyols. In addition, the purified branched polyol molecules can have the structure Y—R(—OH)$_p$, wherein R comprises an amino acid bearing the ionizable functional group —Y, and further comprises one or more hydroxyl-bearing, branched hydrocarbons covalently attached to the amino acid, the hydroxyl-bearing, branched hydrocarbons optionally including one or more ether linkages and bearing a total of p hydroxyl groups, wherein p is at least 4. For example, the amino acid could be lysine, the —Y group could be carboxylic acid, and the branched hydrocarbons could be derived from any of the branched polyols noted herein.

In another embodiment, the branched polyol molecule provided by the invention comprises protected hydroxyl groups and at least one ionizable functional group (preferably a single ionizable functional group), the branched polyol molecule having the structure:

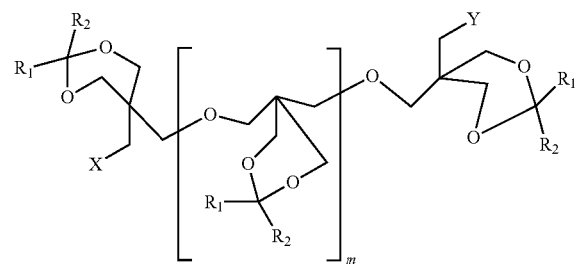

wherein:
R$_1$ and R$_2$ are selected from the group consisting of H, alkyl, substituted alkyl, aryl, substituted aryl, heterocycle, substituted heterocycle, heteroaryl, and substituted heteroaryl, or R$_1$ and R$_2$ together form a cycloalkyl ring, which may be substituted or unsubstituted;

m is 0-20 (e.g., 0-10 or 0-3), preferably 0, 1, 2, 3, 4, 5, 6, 7, 8, 9, or 10;

Y is an ionizable functional group (e.g., carboxylic acid or amine), optionally attached through a linkage and optionally in protected form; and X is a non-ionizable functional group such as hydroxyl.

In yet another aspect, the invention relates to multiarm polymers prepared by the method described herein. The multiarm polymers are characterized by a relatively high purity, which makes the multiarm polymers of the invention particularly well-suited for pharmaceutical applications where high product purity and well-defined product structure are highly desirable properties. In one embodiment, a chromatographically purified multiarm polymer comprising a single ionizable functional group is provided, having the structure Y-POLY'$_{0,1}$-L'$_{0,1}$-R(-L$_{0,1}$-POLY-Z)p, wherein —Y is the single ionizable functional group, L and L' are optional spacer moieties (either the same or different), POLY' is an optional water soluble and non-peptidic polymer, each POLY is a water-soluble and non-peptidic polymer, R is a core molecule, each Z is an independently-selected non-ionizable functional group, and p is at least 2 (e.g., 2-25 or 2-10), preferably 2, 3, 4, 5, 6, 7, 8, 9, or 10 (and further wherein 0 signifies the absence of an element and 1 signifies the presence of the element).

The structure of R will depend on the structure of the polyol core utilized. In one embodiment, R is a branched hydrocarbon, optionally including one or more ether linkages. In another embodiment, R includes a poly(alkylene glycol) chain of 1 to about 25 monomer units at each terminus thereof. Exemplary polyols from which R can be derived include pentaerythritol, oligomers of pentaerythritol, polymers of pentaerythritol, oligomers of glycerol, polymers of glycerol, and sugar-derived polyols. In an alternative embodiment, R comprises an amino acid bearing the ionizable functional group —Y, and further comprises one or more branched hydrocarbons covalently attached to the amino acid, the branched hydrocarbons optionally including one or more ether linkages and including p termini, wherein p is at least 4. For example, the amino acid can be lysine and the —Y group can be carboxylic acid.

The multiarm polymers of the invention can achieve the same levels of purity using the present invention as noted above for the branched polyols. For example, the multiarm polymers of the invention can exhibit a purity of at least about 83%, more preferably at least about 91%, still more preferably at least 95%, yet still more preferably at least 96%, still more preferably at least 97%, yet still more preferably at least 98%, still more preferably at least 99%, and in some cases about 100% purity. As used herein, purity for a given composition refers to the percentage of polymeric species in the composition having the same multiarm arrangement and the same number and type of termini (wherein variations in molecular weight within one standard deviation of the average are not considered to affect purity).

In another aspect, the invention provides conjugates comprising a multiarm polymer of the invention covalently attached to a biologically active molecule. The linkages between the biologically active molecule and the polymer can be degradable (i.e., the conjugate is a prodrug) or stable.

BRIEF DESCRIPTION OF THE DRAWINGS

Figure 1:
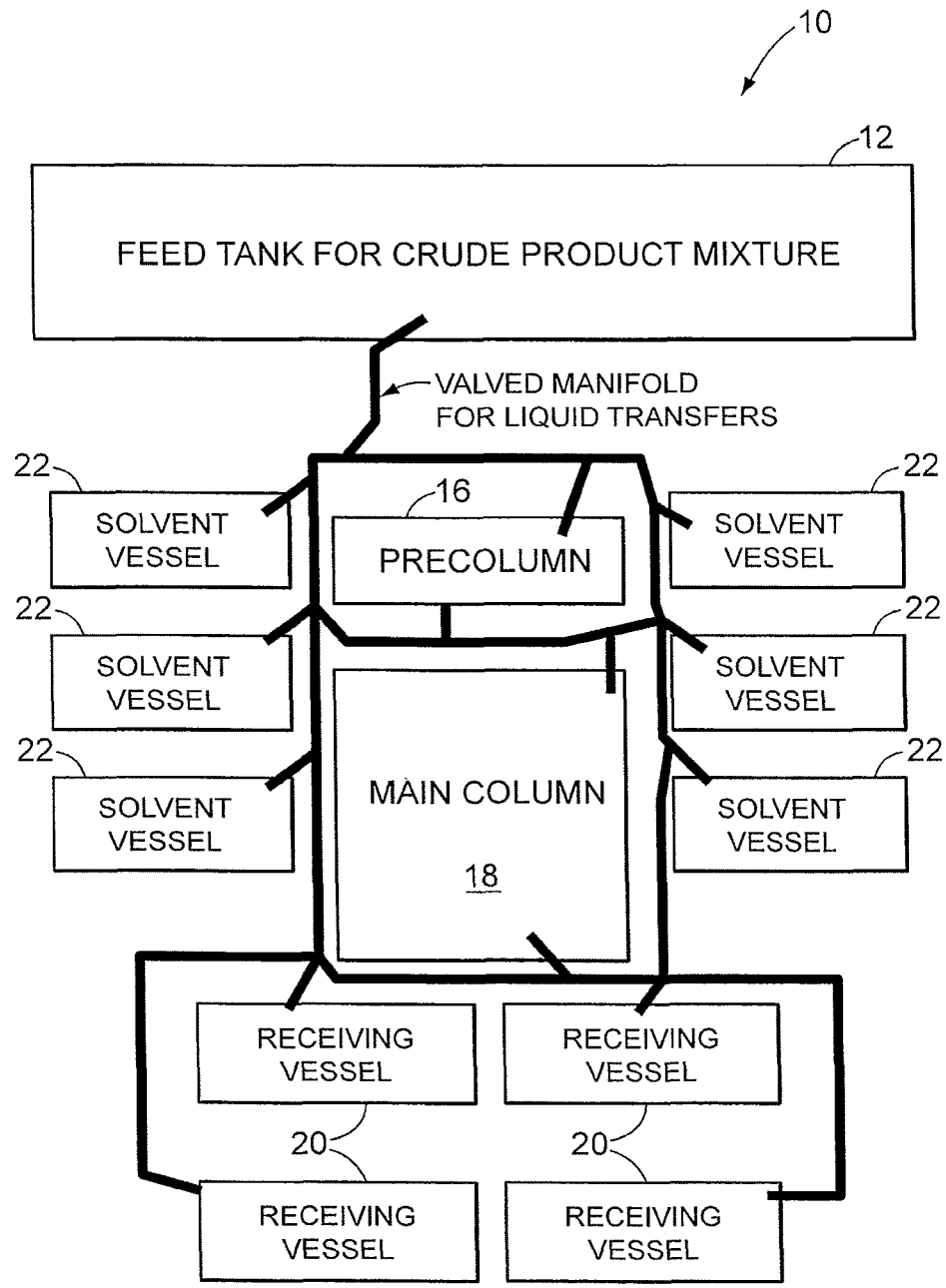
Figure 2:
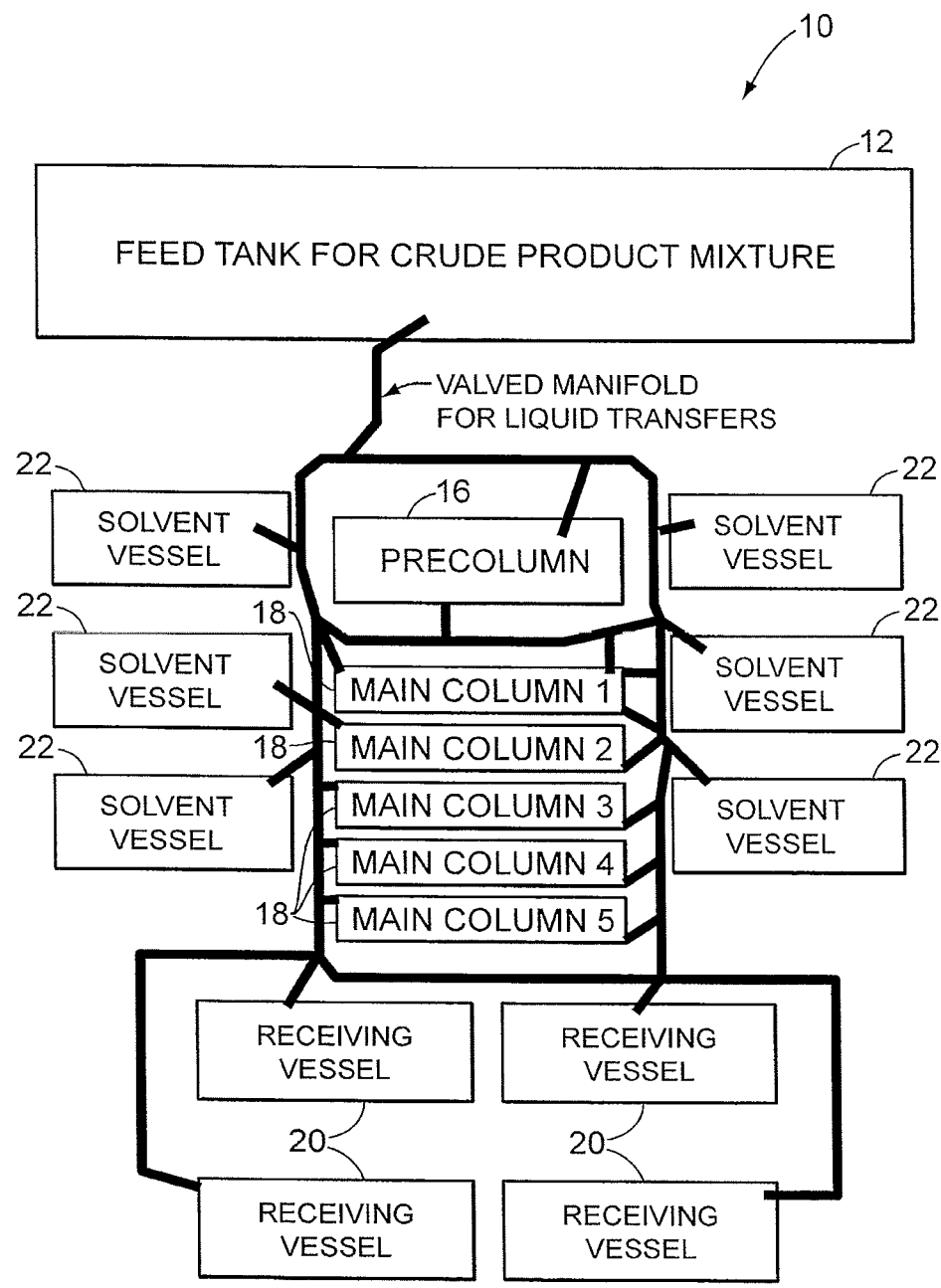
Figure 3:
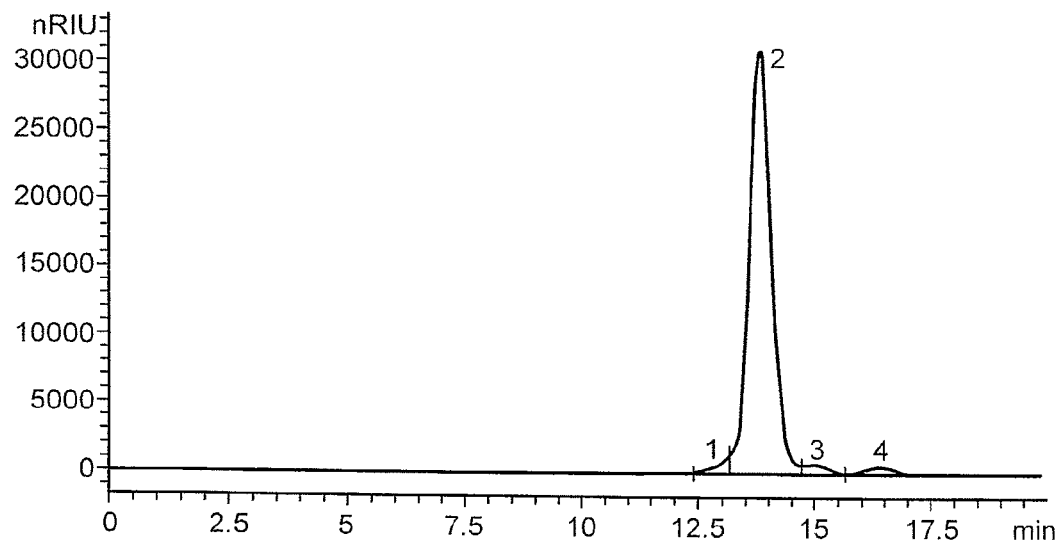

Having thus described the invention in general terms, reference will now be made to the accompanying drawings, wherein:

FIG. 1 illustrates an embodiment of the ion exchange chromatography system in which two columns are employed;

FIG. 2 illustrates a multiple column embodiment of the ion exchange chromatography system;

FIG. 3 is GPC chromatogram of a commercially available 4-ARM-PEG-20 KDa; and

Figure 4:
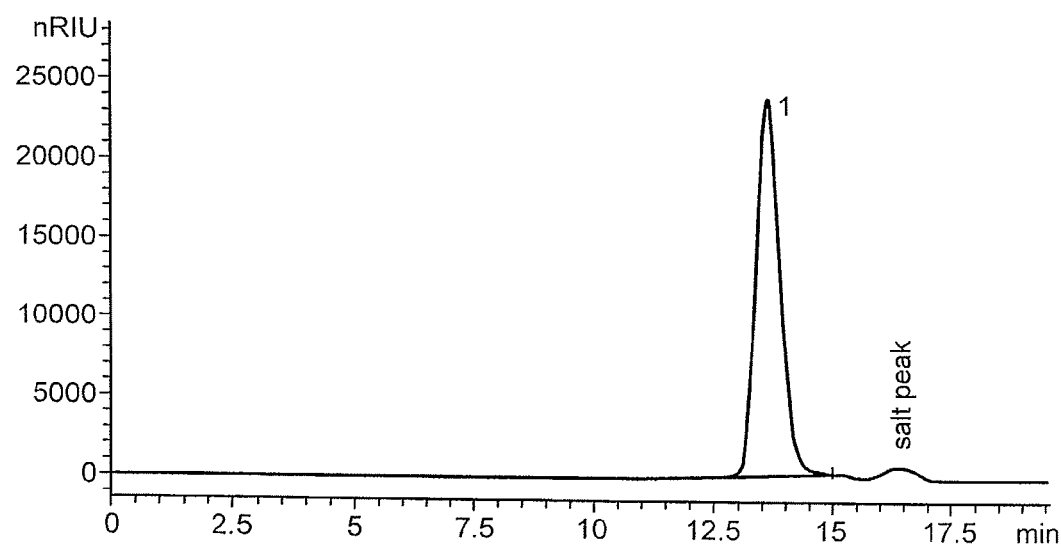

FIG. 4 is GPC chromatogram of the 4-ARM-PEG-20 KDa-mono-butanoic acid made in Example 2.

DETAILED DESCRIPTION OF THE INVENTION

Before describing the present invention in detail, it is to be understood that this invention is not limited to the particular polymers, synthetic techniques, active agents, and the like as such may vary. It is also to be understood that the terminology used herein is for describing particular embodiments only, and is not intended to be limiting.

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

I. Definitions

In describing and claiming the present invention, the following terminology will be used in accordance with the definitions described below.

"PEG," "polyethylene glycol" and "poly(ethylene glycol)" are used herein to mean any water-soluble poly(ethylene oxide). Typically, PEGs for use in the present invention will comprise one of the two following structures: "—O(CH$_2$CH$_2$O)$_n$—" or "—CH$_2$CH$_2$—O—(CH$_2$CH$_2$O)$_n$—CH$_2$CH$_2$—," where n is 3 to 3000, and the terminal groups and architecture of the overall PEG may vary. "PEG" means a polymer that contains a majority, that is to say, greater than 50%, of subunits that are —CH$_2$CH$_2$O—.

One commonly employed PEG is end-capped PEG. When PEG is defined as "—O(CH$_2$CH$_2$O)$_n$—," the end-capping group is generally a carbon-containing group typically comprised of 1-20 carbons and is preferably alkyl (e.g., methyl, ethyl or benzyl) although saturated and unsaturated forms thereof, as well as aryl, heteroaryl, cyclo, heterocyclo, and substituted forms of any of the foregoing are also envisioned. When PEG is defined as "—CH$_2$CH$_2$—O—(CH$_2$CH$_2$O)$_n$—CH$_2$CH$_2$—," the end-capping group is generally a carbon-containing group typically comprised of 1-20 carbon atoms and an oxygen atom that is covalently bonded to the group and is available for covalently bonding to one terminus of the PEG. In this case, the group is typically, alkoxy (e.g., methoxy, ethoxy or benzyloxy) and with respect to the carbon-containing group can optionally be saturated and unsaturated, as well as aryl, heteroaryl, cyclo, heterocyclo, and substituted forms of any of the foregoing. The other ("non-end-capped") terminus is a typically hydroxyl, amine or an activated group that can be subjected to further chemical modification when PEG is defined as "—CH$_2$CH$_2$—O—(CH$_2$CH$_2$O)$_n$—CH$_2$CH$_2$—." In addition, the end-capping group can also be a silane.

Specific PEG forms for use in the invention include PEGs having a variety of molecular weights, structures or geometries (e.g., branched, linear, forked PEGs, multifunctional, and the like), to be described in greater detail below.

The end-capping group can also advantageously comprise a detectable label. When the polymer has an end-capping group comprising a detectable label, the amount or location of the polymer and/or the moiety (e.g., active agent) of interest to which the polymer is coupled to can be determined by using a suitable detector. Such labels include, without limitation, fluorescers, chemiluminescers, moieties used in enzyme labeling, colorimetric (e.g., dyes), metal ions, radioactive moieties, and the like.

The polymers used in the methods described herein are typically polydisperse (i.e., number average molecular weight and weight average molecular weight of the polymers are not equal). The polymers prepared in accordance with the methods described herein, however, possess low polydispersity values—expressed as a ratio of weight average molecular weight (Mw) to number average molecular weight (Mn), (Mw/Mn)—of generally less than about 1.2, preferably less than about 1.15, more preferably less than about 1.10, still more preferably less than about 1.05, yet still most preferably less than about 1.03, and most preferably less than about 1.025.

As used herein, the term "ionizable functional group" and variations thereof is a functional group that may gain or lose a proton by interaction with another ionizable species of a functional group in aqueous or other polar media. Ionizable functional groups include, but are not limited to, amine, carboxylic acids, aldehyde hydrates, ketone hydrates, amides, hydrazines, thiols, phenols, oximes, dithiopyridines, and vinylpyridines.

As used herein, the term "carboxylic acid" is a moiety having a

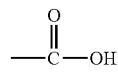

functional group [also represented as a "—COOH" or —C(O)OH], as well as moieties that are derivatives of a carboxylic acid, such derivatives including, for example, protected carboxylic acids. Thus, unless the context clearly dictates otherwise, the carboxylic acid includes not only the acid form, but corresponding esters and protected forms as well. Reference is made to Greene et al., "PROTECTIVE GROUPS IN ORGANIC SYNTHESIS" 3$^{rd}$ Edition, John Wiley and Sons, Inc., New York, 1999.

"Activated carboxylic acid" means a functional derivative of a carboxylic acid that is more reactive than the parent carboxylic acid, in particular, with respect to nucleophilic acyl substitution. Activated carboxylic acids include but are not limited to acid halides (such as acid chlorides), anhydrides, amides and esters.

The term "reactive" or "activated", when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof.

The term "spacer" or "spacer moiety" is used herein to refer to an atom or a collection of atoms optionally used to link interconnecting moieties such as a terminus of a water-soluble polymer and a functional group. The spacer moieties of the invention may be hydrolytically stable or may include a physiologically hydrolyzable or enzymatically degradable linkage.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, 1-methylbutyl, 1-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, iso-butyl, tert-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl (e.g., 0-2 substituted phenyl); substituted phenyl; and the like.

"Substituted aryl" is aryl having one or more non-interfering groups as a substituent. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, benzyloxy, etc.), preferably $C_1$-$C_8$.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Electrophile" refers to an ion or atom or collection of atoms, that may be ionic, having an electrophilic center, i.e., a center that is electron seeking or capable of reacting with a nucleophile.

"Nucleophile" refers to an ion or atom or collection of atoms, that may be ionic, having a nucleophilic center, i.e., a center that is seeking an electrophilic center or capable of reacting with an electrophile.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, orthoesters, and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Multifunctional" or "multisubstituted" in the context of a polymer or polyol of the invention means a polymer or polyol having 2 or more functional groups (e.g., ionizable functional groups) contained therein, where the functional groups may be the same or different. Multifunctional polymers or polyols of the invention will typically contain from about 2-100 functional groups, or from 2-50 functional groups, or from 2-25 functional groups, or from 2-15 functional groups, or from 3 to 10 functional groups, or will contain 2, 3, 4, 5, 6, 7, 8, 9 or 10 functional groups within the polymer backbone or polyol. Thus, multisubstituted (or multifunctional) polymers and polyols include a disubstituted (or difunctional) polymers and polyols.

A "difunctional" or "disubstituted" polymer or polyol means a polymer or polyol having two functional groups contained therein, either the same (i.e., homodifunctional) or different (i.e., heterodifunctional).

A "monofunctional" or "monosubstituted" polymer means a polymer or polyol having a single functional group (e.g., an ionizable functional group) contained therein (e.g., an mPEG based polymer or a polyol with a single —Y group).

A basic or acidic reactant described herein includes neutral, charged, and any corresponding salt forms thereof.

The term "patient," refers to a living organism suffering from or prone to a condition that can be prevented or treated by administration of a conjugate, and includes both humans and animals.

"Optional" or "optionally" means that the subsequently described circumstance may or may not occur, so that the description includes instances where the circumstance occurs and instances where it does not.

Unless otherwise noted, molecular weight is expressed herein as number average molecular weight ($M_n$), which is defined as $$\frac{\sum NiMi}{\sum Ni},$$

wherein Ni is the number of polymer molecules (or the number of moles of those molecules) having molecular weight Mi.

Each of the terms "drug," "biologically active molecule," "biologically active moiety," "active agent" and "biologically active agent", when used herein, means any substance which can affect any physical or biochemical property of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

As used herein, "non-peptidic" refers to a polymer backbone substantially free of peptide linkages. However, the polymer backbone may include a minor number of peptide linkages spaced along the length of the backbone, such as, for example, no more than about 1 peptide linkage per about 50 monomer units.

The term "conjugate" is intended to refer to the entity formed as a result of covalent attachment of a molecule, e.g., a biologically active molecule, to a reactive polymer molecule, preferably a multiarm polymer prepared according to the invention.

"Eluate" refers to a solution that has passed through a chromatography column (i.e., an effluent stream).

"Eluent" refers to the mobile phase utilized during a chromatographic separation.

"Pre-column" and "first column" are used interchangeably herein and refer to a single chromatography column, as well as two or more columns connected in series that serve as the "pre-column" or "first column." In addition, the terms "main column" and "second column" are used interchangeably herein and refer to a single chromatography column, as well as two or more columns connected in series that serve as the "main column" or "second column."

II. Method of Preparing Branched Polymers Using Branched Polyol Starting Material In one aspect, the present invention provides a method of forming branched, functionalized polymeric reagents using branched polyol starting materials, including commercially available crude branched polyol mixtures or crude ethoxylated branched polyol mixtures. The method of the invention involves reacting the branched polyol starting material, which may have one or more of its alcohol groups protected, with a functionalizing reagent comprising an ionizable functional group, —Y. The functionalizing reagent is capable of reacting, in one or more steps, with the polyol to form a plurality of substituted polyols, each comprising a varying number of —Y groups. The reaction is typically carried out under conditions effective to produce a mixture of an unsubstituted branched polyol (i.e., the original branched polyol starting material), a monosubstituted branched polyol (i.e., a polyol having a single —Y group), and one or more multisubstituted branched polyols (e.g., a disubstituted polyol having two —Y groups), preferably characterized by a relatively wide difference in content of the monosubstituted product and the multisubstituted product(s).

The ionizable functional group, —Y, acts as a reactive handle that can be utilized in manipulation and purification of the molecule. Exemplary ionizable functional groups include amine and carboxylic acid groups. Examples of other suitable functional groups include aldehyde hydrate, ketone hydrate, amide, hydrazine, hydrazide, thiol, sulfonic acid, amidate, hydroxylamine, phenol, oxime, alkanoic acids having a carbon length (including the carbonyl carbon) of 1 to about 25 carbon atoms (e.g., carboxymethyl, propanoic acid, and butanoic acid), dithiopyridine, vinylpyridine, 2-substituted-1,3-oxazoline, 2-substituted 1,3-(4H)-dihydrooxazines, 2-substituted-1,3-thiazoline, and 2-substituted 1,3-(4H)-dihydrothiazines.

In order to avoid conversion of most or all of the available hydroxyl groups of the polyol to the ionizable functional group, —Y, the method of the invention preferably comprises converting a portion of the hydroxyl groups to protected hydroxyl groups. This step is particularly advantageous when using larger polyol molecules, such as polyols with 6 or more hydroxyl groups. In certain embodiments, at least about one-third of the available hydroxyl groups are converted to a protected and relatively non-reactive form, preferably at least about one-half, and most preferably at least about two-thirds. Thus, in certain preferred embodiments, no more than about one-third of the available hydroxyl groups are left in unprotected form and, thus, in a form capable of conversion to an ionizable functional group, —Y. In one preferred embodiment utilizing a pentaerythritol oligomer or polymer core, the hydroxyl protecting or blocking step results in conversion of all but two hydroxyl groups into a protected form.

The particular form of the hydroxyl protecting group may vary without departing from the present invention. Any protecting group known in the art can be utilized. Exemplary hydroxyl protecting groups include cyclic acetal groups, cyclic ketal groups, esters, and certain activated ethers, such as benzyl, benzhydryl, trityl, trialkylsilyl and methoxymethyl ethers.

Following optional protection of a portion of the hydroxyl groups of the polyol starting material, the functionalization reaction can be performed. For purposes of illustrating one or more advantages of the invention, a pentaerythritol oligomer or polymer core starting material (a "pentaerythritol-based core molecule") is considered as having two available hydroxyl groups with the remainder in protected form. Commencement of a reaction of the pentaerythritol-based core molecule with a functionalizing reagent comprising an amine or carboxylic acid (optionally in protected form) will result in formation of a monosubstituted polyol species (e.g., a polyol having a single protected or free amine or protected or free carboxylic acid group) and a multisubstituted polyol species, such as a disubstituted polyol species (e.g., a polyol having two protected or free amine or protected or free carboxylic acid groups). As the number of moles of the mono- and multisubstituted polyols increases, the number of moles of the original polyol starting material will decrease concomitantly.

In one or more embodiments of the present invention, the reaction is allowed to proceed until a certain predetermined amount of the monosubstituted and multisubstituted polyol species is formed. This predetermined amount is selected based on the disparity in concentration of the monosubstituted product and the multisubstituted product. By stopping the reaction at a point characterized by a large difference in concentration of the monosubstituted product and the multisubstituted product, separation or purification of the polyol mixture is made more efficient. The protected hydroxyl groups can be deprotected using techniques known in the art at any point in the process following the functionalizing reaction without departing from the invention.

The mixture of polyol products is subjected to a purification step in order to separate the mixture components and provide a monosubstituted polyol substantially free from the unsubstituted and multisubstituted polyol species. By performing the purification/separation process while the desired monosubstituted polyol and the multisubstituted polyol species are present at differing concentrations, separation is made easier and formation of highly pure monofunctional polyol reagents is possible. The approach of the present invention is particularly well suited for use with functionalizing reagents that attach ionizable functional groups to the polymer and separation processes adapted for separation based on differences in charge, such as ion exchange chromatography.

Once separated into highly pure fractions, any of the monosubstituted or multisubstituted polyols can be used in further process steps to form multiarm polymeric reagents that can be used, for example, to foam conjugates with biologically active agents. For example, in one embodiment, PEG polymer or oligomer segments are attached to the purified monosubstituted polyol product at the site of the hydroxyl groups (following deprotection if necessary) to form a multiarm PEG polymer reagent, and the terminus of each polymer arm is functionalized for reaction with a biologically active agent. It is noted that the attachment of the polymer aims can proceed in any manner known in the art, such as by ethoxylation (e.g., base-catalyzed reaction of the polyol with ethylene oxide or oxirane) or attachment of a preformed polymer segment via a nucleophilic substitution or nucleophilic addition reaction. Attaching a preformed polymer segment to the polyol core is typically preferred where it is desirable for each polymer arm to have the same molecular weight. In one embodiment, preformed polymer segments are attached to the polyol core by reaction of the polyol with N,N'-disuccinimidyl carbonate (DSC) followed by reaction with an amine-terminated polymer, such as an amine-terminated PEG, thereby resulting in attachment of the polymer to the polyol core at the site of each hydroxyl group via a urethane linkage. Other functional groups on the polyol and the polymer segments could be used without departing from the present invention. The linkage between the polyol core and the polymer segments will depend on the functional groups selected and may be hydrolytically stable or unstable. It is not necessary to attach the polymer arms after the functionalizing and purifying steps discussed above. Instead, in certain embodiments, the polymer arms are attached to the polyol core at the site of the hydroxyl groups prior to the functionalizing reaction. In such embodiments, the functional groups at the terminus of each polymer arm should be in protected form (e.g., a protected hydroxyl) prior to the functionalizing reaction. Further, it is noted that in certain embodiments, the commercially available starting material will already include polymeric arms, such as in the case of certain ethoxylated polyol mixtures.

As noted above, further functionalization of the polymer arms of the multiarm polymer structure can be carried out by subjecting the purified polymeric reagent to additional reaction steps to form other useful active polymeric reagents, such as the formation of active esters from carboxylic acid terminated polymers or the formation of maleimides from amine terminated polymers.

Examples of suitable functional groups that can be formed on the final purified polymer include hydroxyl, active ester (e.g., N-hydroxysuccinimidyl ester and 1-benzotriazolyl ester), active carbonate (e.g., N-hydroxysuccinimidyl carbonate, 1-benzotriazolyl carbonate, and p-nitrophenyl carbonate), acetal, aldehyde having a carbon length of 1 to 25 carbons (e.g., acetaldehyde, propionaldehyde, and butyraldehyde), aldehyde hydrate, alkenyl, acrylate, methacrylate, acrylamide, active sulfone, amine, hydrazide, thiol, alkanoic acids having a carbon length (including the carbonyl carbon) of 1 to about 25 carbon atoms (e.g., carboxylic acid, carboxymethyl, propanoic acid, and butanoic acid), acid halide, isocyanate, isothiocyanate, maleimide, vinylsulfone, dithiopyridine, vinylpyridine, iodoacetamide, epoxide, glyoxal, dione, mesylate, tosylate, and tresylate. Exemplary functional groups are discussed in the following references: N-succinimidyl carbonate (see e.g., U.S. Pat. Nos. 5,281,698 and 5,468,478), amine (see, e.g., Buckmann et al. Makromol. Chem. 182:1379 (1981), and Zalipsky et al. Eur. Polym. J. 19:1177 (1983)), hydrazide (see, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (see, e.g., Abuchowski et al. Cancer Biochem. Biophys. 7:175 (1984) and Joppich et al., Makromol. Chem. 180:1381 (1979)), succinimidyl ester (see, e.g., U.S. Pat. No. 4,670, 417), benzotriazole carbonate (see, e.g., U.S. Pat. No. 5,650, 234), glycidyl ether (see, e.g., Pitha et al. Eur. J. Biochem. 94:11 (1979), and Elling et al., Biotech. Appl. Biochem. 13:354 (1991)), oxycarbonylimidazole (see, e.g., Beauchamp et al., Anal. Biochem. 131:25 (1983), and Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. Nos. 5,824,784 and 5,252,714), maleimide (see, e.g., Goodson et al. Bio/Technology 8:343 (1990), Romani et al. in Chemistry of Peptides and Proteins 2:29 (1984), and Kogan, Synthetic Comm. 22:2417 (1992)), orthopyridyl-disulfide (see, e.g., Woghiren et al. Bioconj. Chem. 4:314 (1993)), acrylol (see, e.g., Sawhney et al., Macromolecules, 26:581 (1993)), vinylsulfone (see, e.g., U.S. Pat. No. 5,900,461). All of the above references are incorporated herein by reference.

Thus, using the method of the invention outlined above, readily available multiarm polyol core molecules may be converted into core molecules having sufficient purity for pharmaceutical use. Two exemplary embodiments of the method of the invention are illustrated schematically in Scheme 1a and 1b below. In Scheme 1a, a polyol core molecule with a carboxylic acid group is shown, and in Scheme 1b, a polyol core molecule functionalized with an amine (i.e., a basic group) is shown. Either type of molecule is readily purified using ion exchange chromatography as explained in greater detail below.

Scheme 1a

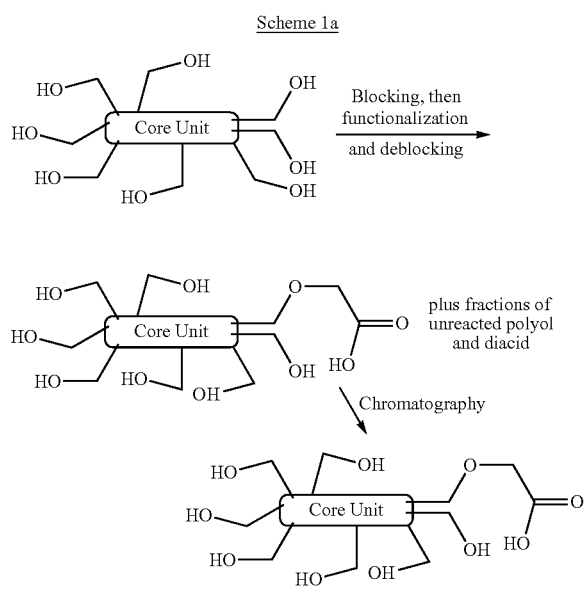

The "Core Unit" block in Scheme 1a (and Scheme 1b below) represents the branched hydrocarbon portion of the polyol molecule, which may optionally include one or more ether linkages or polymeric arm segments (e.g., where the starting material is ethoxylated) as explained in greater detail below. As shown in Scheme 1a, the core molecule is subjected to a hydroxyl protecting step followed by functionalization with a carboxylic acid group and deblocking or deprotecting of the hydroxyl groups. The resulting mixture of products includes a polyol with a single carboxylic acid, as well as unreacted polyol and a diacid comprising two carboxylic acid groups. The mixture is subjected to ion exchange chromatography in order to separate the monosubstituted polyol from the unsubstituted polyol and the disubstituted (in this case, diacid) polyol.

Scheme 1b

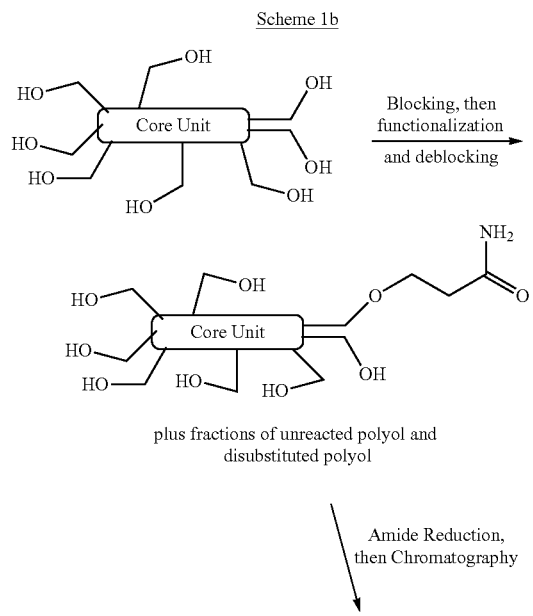

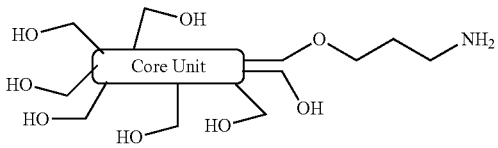

Scheme 1b above is substantially identical to Scheme 1a, except the functionalization reaction results in addition of an amide group that can be readily reduced to form an amine group. As in Scheme 1a, the functionalizing step results in a mixture of products including the unreacted polyol, a monosubstituted polyol with one amide group, and a disubstituted polyol with two amide groups. Following ion exchange chromatography, the monosubstituted product can be separated from the remaining species in high purity.

An exemplary chromatographically purified branched polyol of the invention will comprise a single ionizable functional group and two or more hydroxyl groups. As used herein, the term "chromatographically purified" means purified by ion exchange chromatography based on the number of ionizable functional groups on each molecule as described herein. Alternatively, the purified branched polyol could be a multisubstituted polyol comprising two or more —Y ionizable groups following separation from monosubstituted and unsubstituted polyol components of the initial mixture.

The purified branched polyol of the invention can, for example, have the structure Y—R(—OH)$_p$, wherein R is a branched hydrocarbon, optionally including one or more ether linkages, and p is at least 2 (e.g., 3 to about 25 or 3 to about 10). The R group can include a poly(alkylene glycol) chain of 1 to about 25 monomer units attached to each terminal hydroxyl group. The purified polyol can be derived from a variety of polyol cores such as pentaerythritol, oligomers of pentaerythritol, polymers of pentaerythritol, oligomers of glycerol, polymers of glycerol, and sugar-derived polyols. Exemplary branched polyols of this type are set forth in Schemes 2 and 3 below.

In addition, the branched polyol can have the structure Y—R(—OH)$_p$, wherein R comprises an amino acid bearing the ionizable functional group —Y, and further comprises one or more hydroxyl-bearing, branched hydrocarbons covalently attached to the amino acid, the hydroxyl-bearing, branched hydrocarbons optionally including one or more ether linkages and bearing a total of p hydroxyl groups, wherein p is at least 4. For example, the amino acid could be lysine and the —Y group could be carboxylic acid, as set forth in Schemes 6 and 7 below.

As noted above, the monosubstituted products of Schemes 1a and 1b can be manipulated further as needed to form highly pure multiarm polymeric reagents suitable for use in forming conjugates with biologically active molecules. Exemplary conjugate structures are shown below using an exemplary 8-arm polyol core. Where the reactive handle (i.e., the ionizable functional group) is added prior to attachment of polymeric arms, the resulting conjugate can have the following structure:

Where the polymeric units are already in place prior to adding the reactive handle, such as in the case of an ethoxylated polyol starting material, the resulting 8-arm conjugate can have the following structure:

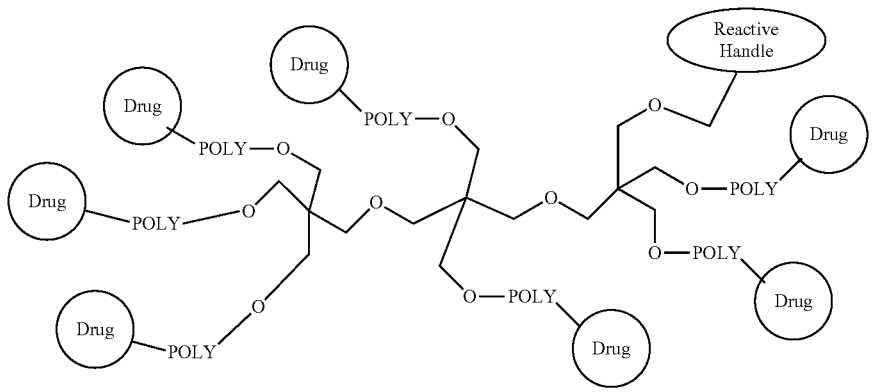

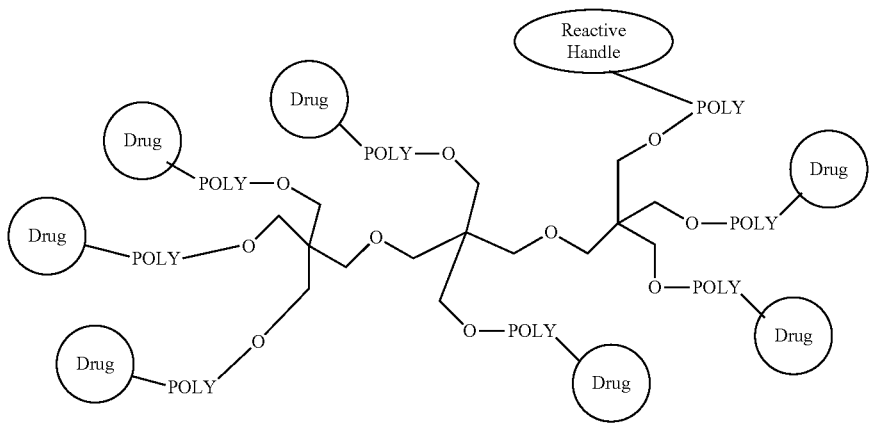

The multiarm polymers provided by the invention are characterized by a relatively high purity, making them particularly well-suited for pharmaceutical applications where a high degree of purity and structural consistency is needed. The purified and isolated multiarm polymers can include a single ionizable group (i.e., polymers derived from the monosubstituted polyol component of the initial unpurified polyol mixture) or two or more ionizable groups (i.e., polymers derived from the multisubstituted polyol components of the initial unpurified polyol mixture). In one preferred embodiment, a chromatographically purified multiarm polymer comprises a single ionizable functional group and has the structure Y-POLY'$_{0,1}$-L'$_{0,1}$-R(-L$_{0,1}$-POLY-Z)p, wherein —Y is the single ionizable functional group, L and L' are optional spacers such as any of the spacers set forth below, POLY' is an optional water soluble and non-peptidic polymer, each POLY is a water-soluble and non-peptidic polymer, R is a core molecule such as a core derived from a polyol starting material as described in greater detail below, each Z is an independently-selected non-ionizable functional group such as hydroxyl or a protected, non-ionizable form of an ionizable functional group, and p is at least 2 (e.g., 2-25 or 2-10), preferably 2, 3, 4, 5, 6, 7, 8, 9, or 10.

The structure of R of the multiarm polymer will depend on the structure of the polyol core utilized. In one embodiment, R is a branched hydrocarbon, optionally including one or more ether linkages. In another embodiment, R includes a poly(alkylene glycol) chain of 1 to about 25 monomer units at each terminus thereof. Exemplary polyols from which R can be derived include pentaerythritol, oligomers of pentaerythritol, polymers of pentaerythritol, oligomers of glycerol, polymers of glycerol, and sugar-derived polyols. In an alternative embodiment, R comprises an amino acid bearing the ionizable functional group —Y, and further comprises one or more branched hydrocarbons covalently attached to the amino acid, the branched hydrocarbons optionally including one or more ether linkages and including p termini, wherein p is at least 4. The amino acid can be, for example, lysine and the —Y group can be carboxylic acid, as set forth in Reaction Schemes 6 and 7.

The invention includes conjugates comprising a multiarm polymer of the invention covalently attached to at least one biologically active molecule, preferably two or more biologically active molecules. In certain embodiments, the number of biologically active molecules will be 2 to about 25, more preferably about 3 to about 10 (e.g., 2, 3, 4, 5, 6, 7, 8, 9, or 10). The linkage between the biologically active molecule and the polymer can be degradable (i.e., the conjugate is a prodrug) or stable. In certain preferred embodiments, the conjugate results from attachment of one or more biologically active molecules to a purified multiarm polymer comprising a single ionizable group. However, the conjugate can also result from attachment of biologically active molecules to derivatives of such polymers, such as derivatives where the ionizable functional group is converted to a different functional group, such as hydroxyl, so that the polymer no longer contains any ionizable functional groups, or derivatives comprising more than one ionizable functional group (i.e., one or more of the nonionizable functional groups such as hydroxyl groups is converted to an ionizable functional group such as an amine or carboxylic acid). Further, in certain embodiments, the conjugates are formed by reaction of biologically active molecules with multiarm polymers containing two or more ionizable functional groups or derivatives thereof.

The total molecular weight of the water-soluble and non-peptidic polymer portion of the multiarm polymer can vary, but is typically from about 44 Da to about 100,000 Da. In certain embodiments, the total water-soluble polymer molecular weight of the multiarm polymer is from about 1,000 Da to about 80,000 Da, more preferably about 2,000 Da to about 40,000 Da, and most preferably about 3,000 to about 35,000 Da. Other exemplary ranges include about 5,000 to about 30,000 Da, about 7,500 Da to about 25,000 Da, and about 10,000 to about 20,000 Da. Certain multiarm polymers made using the inventive method can have a total polymer molecular weight of about 44 Da, 100 Da, 200 Da, 300 Da, 400 Da, 500 Da, 600 Da, 700 Da, 800 Da, 900 Da, 1,000 Da, 1,500 Da, 2,000 Da, 3,000 Da, 4,000 Da, 5,000 Da, 6,000 Da, 7,500 Da, 10,000 Da, 12,000 Da, 15,000 Da, 17,500 Da, 20,000 Da, 22,500 Da, 25,000 Da, 27,500 Da, 30,000 Da, 32,500 Da, 35,000 Da, 37,500 Da, 40,000 Da, 42,500 Da, 45,000 Da, 47,500 Da, 50,000 Da, 52,500 Da, 55,000 Da, 57,500 Da, 60,000 Da, 62,500 Da, 65,000 Da, 67,500 Da, 70,000 Da, 72,500 Da, 75,000 Da, 77,500 Da, and 80,000 Da.

A. Polyol Starting Materials

The polyol used in the process of the invention is a molecule comprising a plurality of available hydroxyl groups. Depending on the desired number of polymer arms, the polyol will typically comprise 3 to about 25 hydroxyl groups, preferably about 3 to about 22 hydroxyl groups, most preferably about 5 to about 12 hydroxyl groups. Although the spacing between hydroxyl groups will vary from polyol to polyol, there are typically 1 to about 20 atoms, such as carbon atoms, between each hydroxyl group, preferably 1 to about 5. The particular polyol chosen will depend on the desired number of hydroxyl groups needed as attachment sites for the polymer arms. The weight average molecular weight of the polyol starting material is typically between about 100 to about 2,000 Da. The polyol typically has a branched structure, meaning one or more carbon atoms in the hydrocarbon core structure of the polyol are covalently attached to three or four atoms selected from carbon atoms and ether-linked oxygen atoms (i.e., oxygen atoms attached to two carbon atoms).

Preferred polyols include glycerol oligomers or polymers such as hexaglycerol, pentaerythritol and oligomers or polymers thereof (e.g., dipentaerythritol, tripentaerythritol, tetrapentaerythritol, and ethoxylated forms of pentaerythritol), and sugar-derived alcohols such as sorbitol, arabanitol, and mannitol. Also, many commercially available polyols containing ionizable groups, such as 2-amino-2-(hydroxymethyl)-1,3-propanediol (TRIS), 2-[bis(2-hydroxyethylpamino]-2-(hydroxymethyl)-1,3-propanediol, {[2-hydroxy-1,1-bis(hydroxymethyl)ethyl]amino}acetic acid (Tricine), 2-[(3-{[2-hydroxy-1,1-bis(hydroxymethyl)ethyl]amino}propyl)amino]-2-(hydroxymethyl)-1,3-propanediol, 2-{[2-hydroxy-1,1-bis(hydroxymethyl)ethyl]amino}ethanesulfonic acid (TES), 4-{[2-hydroxy-1,1-bis(hydroxymethyl)ethyl]amino}-1-butanesulfonic acid, and 2-[bis(2-hydroxyethyl)amino]-2-(hydroxymethyl)-1,3-propanediol hydrochloride are appropriate starting materials. When such polyols are used, the step by which an ionizable group is added may be avoided. In some cases, however, the ionizable group or groups must be protected or modified prior to proceeding with the method. Typically, polymeric polyols used in the present invention will comprise no more than about 25 monomer units. The structures of dipentaerythritol and tripentaerythritol are provided below along with one of the structures possible for hexaglycerol.

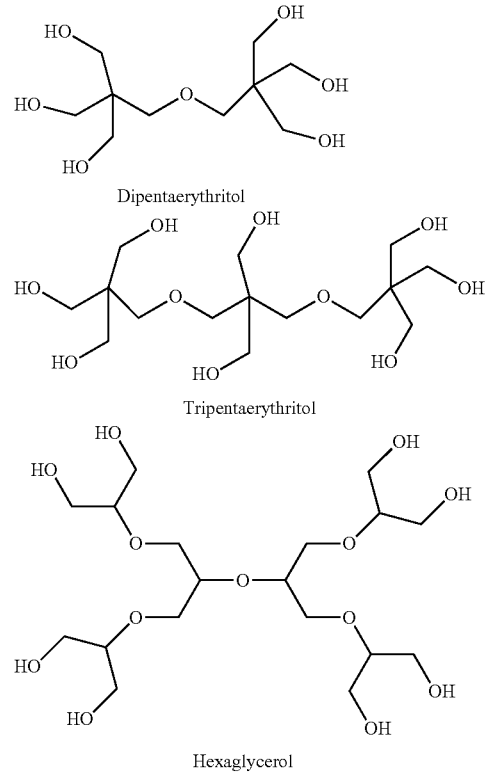

Dipentaerythritol

Tripentaerythritol

Hexaglycerol

Hydroxypropyl-β-cyclodextrin, which has 21 available hydroxyl groups, is another exemplary polyol. Yet another exemplary polyol is a hyperbranched polyglycerol available from Hyperpolymers GmbH of Freiburg, Germany, which is shown below.

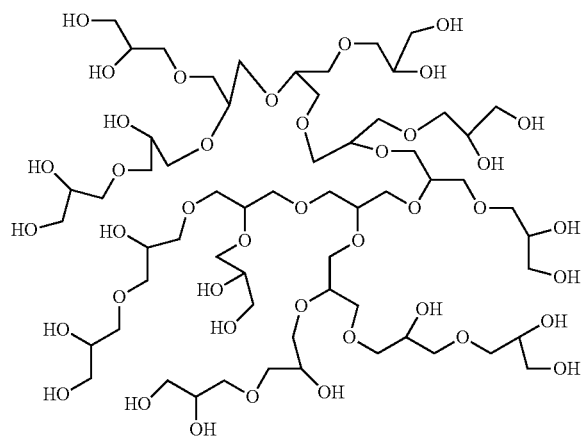 [SMILES: OCC(O)COCC(O)COCC(COCC(COC(COCC(O)CO)COC(COCC(O)CO)COCC(COCC(O)CO)OCC(COCC(O)CO)OCC(O)COCC(O)CO)OCC(COCC(O)COCC(O)CO)OCC(O)COCC(O)CO)OCC(O)CO]

The polyol may include PEG or other poly(alkylene glycol) oligomer or polymer segments attached to the polyol core. The polyol starting material is typically in the form of a mixture of products, such as a mixture of polyol oligomers or polymers of different molecular weights or a mixture of ethoxylated polyol structures of different molecule weight, possibly further comprising a residual amount of the original polyol monomeric unit, such as glycerol. However, at least one of the polyols in the starting mixture is typically a branched polyol having at least three available hydroxyl groups according to the formula R(OH)$_p$, wherein R is a branched hydrocarbon, optionally including one or more ether linkages, and p is at least 3, typically 3 to about 25, and preferably 3 to about 10. The branched polyol molecule preferably comprises a branched hydrocarbon, R, comprising at least one ether linkage and from about 5 to about 100 total carbon and oxygen atoms. In certain embodiments, the branched polyol includes poly(alkylene glycol) chains (e.g., PEG chains) of 1 to about 25 monomer units attached to the terminal hydroxyl groups, preferably 1 to about 20 monomer units, and most preferably 1 to about 15 monomer units.

Polyols having closely-spaced hydroxyl groups are particularly preferred in certain embodiments of the invention where the hydroxyl protecting groups are cyclic acetal or ketal groups. A spacing of two or three carbon atoms between hydroxyl groups within the polyol structure enables the formation of certain preferred heterocyclic protecting groups. For example, the close spacing between hydroxyl groups of pentaerythritol oligomers or polymers enable the formation of cyclic acetal or ketal groups using techniques known in the art. The cyclic acetal or ketal groups can be formed by reacting the polyol with an aldehyde reagent, such as a reagent having the formula R'—CHO, wherein R' is alkyl, substituted alkyl, aryl, or substituted aryl, or a ketone reagent (e.g., cyclohexanone). An exemplary aldehyde reagent is benzaldehyde. Using a pentaerythritol oligomer or polymer core as an example, the structure resulting from the reaction with an aldehyde reagent is shown below.

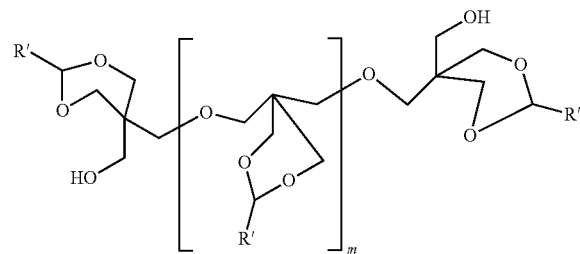

wherein R' is as defined above and m is 0-20.

Thus, the invention provides branched polyol molecules comprising protected hydroxyl groups and at least one ionizable functional group (preferably a single ionizable functional group), the branched polyol molecule having the structure:

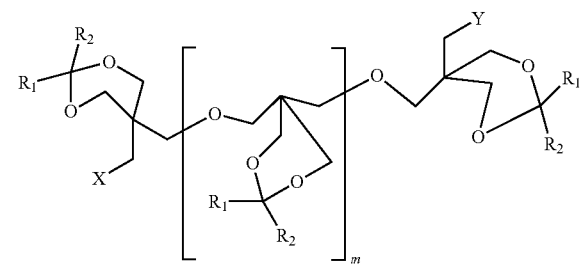

wherein:

$R_1$ and $R_2$ are selected from the group consisting of H, alkyl, substituted alkyl, aryl, substituted aryl, heterocycle, substituted heterocycle, heteroaryl, and substituted heteroaryl, or $R_1$ and $R_2$ together form a cycloalkyl ring, which may be substituted or unsubstituted;

m is 0-20, preferably 1-10 (e.g., 1, 2, 3, 4, 5, 6, 7, 8, 9, or 10), more preferably 1-3;

Y is an ionizable functional group (e.g., carboxylic acid or amine), optionally attached through a linkage and optionally in protected form; and X is Y or a non-ionizable functional group such as hydroxyl or protected forms of ionizable functional groups. Other non-ionizable functional groups can be used.

In another example of a hydroxyl protecting reaction using an aldehyde reagent, the hyperbranched polyglycerol shown above is reacted with an aldehyde reagent in the reaction scheme shown below.

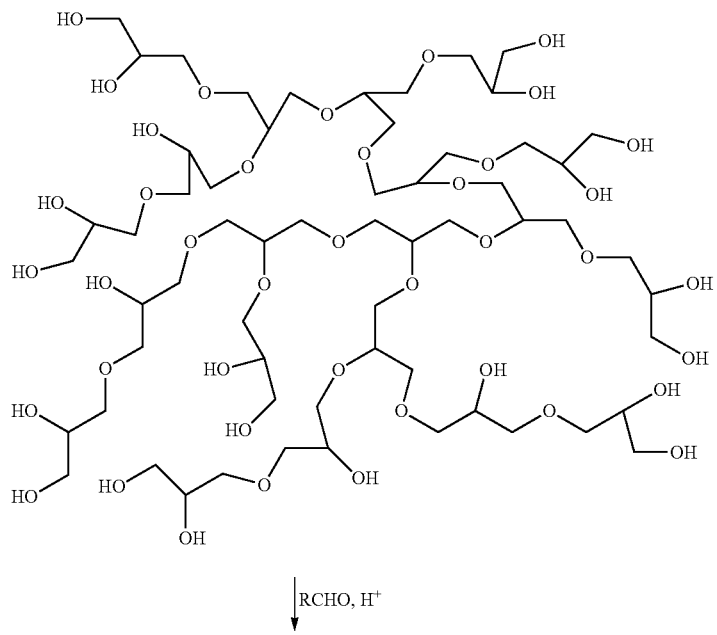

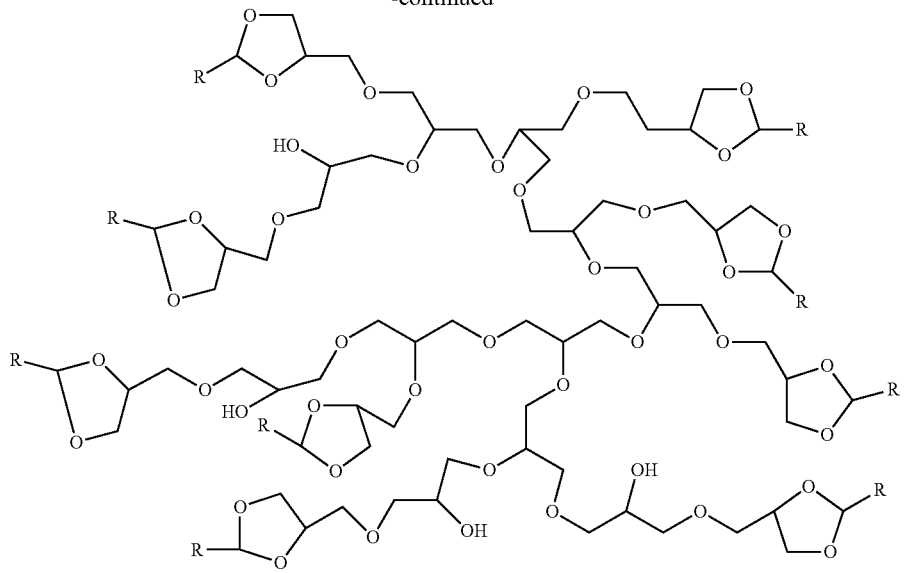

The polyol is typically dissolved in water or an organic solvent prior to the functionalizing reaction discussed below. Any organic solvent compatible with polyols of the type used in the present invention can be utilized, such as toluene, xylene, benzene, dichloromethane, chloroform, acetonitrile, tetrahydrofuran, or acetone. Mixtures of the above solvents or other similar solvents known in the art also can be used.

B. Water-Soluble and Non-Peptidic Polymers

The key to use of multiarm delivery systems is the presence of one or more polymer segments that provide the special drug delivery properties discussed earlier. If the polyol has one or more of the hydroxyl groups near to one another, as pointed out above, this may be an advantage when protecting these groups but it is generally a negative factor when attaching drug molecules for delivery. Chain extenders, which may be oligomeric or polymeric units, reduce the complications of attachment of the ultimate drug molecule and may reduce complications of drug delivery. Thus the preferred reagent prepared by this method will have oligomeric or polymeric chain extenders between the core molecule and the reactive end groups to which drug molecules are attached.

It is possible to provide multiarm polymers wherein the terminus of each arm is relatively remote from the core. One may accomplish this by attaching heterobifunctional polymers, such as heterobifunctional polymer PEGs of the type described in U.S. Pat. No. 6,448,369 to the various hydroxyl groups on the core.

The water-soluble and non-peptidic polymer segments attached to the polyol core should be non-toxic and biocompatible, meaning that the polymer is capable of coexistence with living tissues or organisms without causing harm. It is to be understood that the polymer can be any of a number of water soluble and non-peptidic polymers, such as those described herein as suitable for use in the present invention. Preferably, poly(ethylene glycol) (i.e., PEG) is the polymer used to form the polymeric aims of the multiarm structures formed according to the present invention. The term PEG includes poly(ethylene glycol) in any of a number of geometries or forms, including linear forms, branched or multi-arm forms (e.g., forked PEG or PEG attached to a polyol core), pendant PEG, or PEG with degradable linkages therein, to be more fully described below.

Multiarm or branched PEG molecules, such as those described in U.S. Pat. No. 5,932,462, which is incorporated by reference herein in its entirety, can also be used as the PEG polymer. Generally speaking, a multiarm or branched polymer possesses two or more polymer "arms" extending from a central branch point (e.g., C in Formula II below). For example, an exemplary branched PEG polymer has the structure:

Formula I

wherein $PEG_1$ and $PEG_2$ are PEG polymers in any of the forms or geometries described herein, and which can be the same or different, and L' is a hydrolytically stable linkage. An exemplary branched PEG of Formula I has the structure:

Formula II

wherein: $poly_a$ and $poly_b$ are PEG backbones, such as methoxy poly(ethylene glycol); R" is a nonreactive moiety, such as H, methyl or a PEG backbone; and P and Q are nonreactive linkages. In a preferred embodiment, the branched PEG polymer is methoxy poly(ethylene glycol) disubstituted lysine.

The branched PEG structure of Formula II can be attached to a third oligomer or polymer chain as shown below:

Formula III

wherein PEG$_3$ is a third PEG oligomer or polymer chain, which can be the same or different from PEG$_1$ and PEG$_2$.

The PEG polymer may alternatively comprise a forked PEG. Generally speaking, a polymer having a forked structure is characterized as having a polymer chain attached to two or more functional groups via covalent linkages extending from a hydrolytically stable branch point in the polymer. An example of a forked PEG is represented by PEG-L-CHY$_2$, where L is a linking group and Y is a functional group. Each Y group is linked to CH by a chain of atoms of defined length. U.S. Pat. No. 6,362,254, the contents of which are incorporated by reference herein, discloses various forked PEG structures capable of use in the present invention. The chain of atoms linking the Y functional groups to the branching carbon atom serve as a tethering group and may comprise, for example, an alkyl chain, ether linkage, ester linkage, amide linkage, or combinations thereof.

As noted above, the PEG polymer may comprise a pendant PEG molecule having reactive groups, such as hydroxyl, covalently attached along the length of the PEG backbone rather than at the end of the PEG chain. The pendant reactive groups can be attached to the PEG backbone directly or through a linking moiety, such as an alkylene group.

In addition to the above-described forms of PEG, the polymer can also be prepared with one or more hydrolytically stable or degradable linkages in the polymer backbone, including any of the above described polymers. For example, PEG can be prepared with ester linkages in the polymer backbone that are subject to hydrolysis. As shown below, this hydrolysis results in cleavage of the polymer into fragments of lower molecular weight:

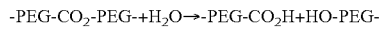

Other hydrolytically degradable linkages, useful as a degradable linkage within a polymer backbone, include carbonate linkages; imine linkages resulting, for example, from reaction of an amine and an aldehyde (see, e.g., Ouchi et al., Polymer Preprints, 38(1):582-3 (1997), which is incorporated herein by reference); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; and oligonucleotide linkages formed by, for example, a phosphoramidite group, e.g., at the end of a polymer, and a 5' hydroxyl group of an oligonucleotide.

It is understood by those skilled in the art that the term poly(ethylene glycol) or PEG represents or includes all the above forms of PEG.

Any of a variety of other polymeric polyols comprising other non-peptidic and water soluble polymer chains can also be used in the present invention. The polymer arms of the multiarm structure made according to the invention can be linear, or can be in any of the above-described forms (e.g., branched, forked, and the like). Examples of suitable polymers include, but are not limited to, other poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof.

Different polymers can be incorporated into the same polymer backbone. For example, one or more of the PEG molecules in the branched structures shown in Formulas I-III can be replaced with a different polymer type. Any combination of water soluble and non-peptidic polymers is encompassed within the present invention.

The molecular weight of each of the polymer segments or arms incorporated into the multiarm polymer structure will vary depending on the desired application, the configuration of the polymer structure, the degree of branching, and the like. Generally, the molecular weight of each polymer arm within the multiarm structures made according to the invention will be about 44 Da to about 100,000 Da, preferably about 1,000 Da to about 80,000 Da, and more preferably about 2,000 Da to about 40,000 Da. Exemplary polymer segment embodiments have a molecular weight of approximately 44 Da, 100 Da, 200 Da, 300 Da, 400 Da, 500 Da, 600 Da, 700 Da, 800 Da, 900 Da, 1,000 Da, 1,500 Da, 2,000 Da, 3,000 Da, 4,000 Da, 5,000 Da, 7,500 Da, 10,000 Da, 15,000 Da, 20,000 Da, 25,000 Da, 30,000 Da, 35,000 Da, and 40,000 Da.

C. Functionalizing Reaction

The reaction step or steps used to react a functionalizing reagent with the polyol can vary depending on a number of factors, including the type of functional group involved, the type and configuration of the polyol, and so forth. The exact nature of the reaction sequence is not critical to the present invention and any known method of functionalizing polyols of the type used in the present invention can be utilized without departing from the invention.

As noted above, in one embodiment, the functionalizing reaction is only allowed to proceed under conditions effective to produce a product mixture characterized by a wide difference in the concentrations of the monosubstituted product and the di- or other multisubstituted products. Preferably, the reaction is also conducted under conditions effective to produce a relatively low content of multisubstituted product. To achieve the desired content disparity, the reaction between the polyol starting material and the functionalizing reagent can be stopped or quenched at the appropriate time using any method known in the art, such as by rapidly changing process parameters (e.g., temperature or degree of mixing) or by carefully controlling the amount of reactants, thereby controlling the reaction on a stoichiometric basis. The appropriate time for stopping or quenching the reaction can be determined by obtaining periodic samples of the reaction mixture and determining the amount of species present (e.g., by chromatographic methods, NMR methods and so forth) or by measuring a parameter (e.g., pH) known to correlate with the amount of species present. Alternatively, if a significant deficiency of the functionalizing reagent is charged, the reaction will only proceed to partial conversion of the diol. In this instance, the reaction may be allowed to proceed to completion.

The reaction is generally performed under conditions effective to form no more than about 50 percent of the multisubstited polyol. Reactions allowed to continue past this point result in multisubstituted polyol being present in an amount greater than monosubstituted polyol, with the result that separation becomes increasingly inefficient. While no more than about 50 percent of the multisubstituted polyol is typically allowed to form, it is often preferred that the percent of multisubstituted polyol formation is encompassed in one or more of the following ranges: no more than about 40 percent; no more than about 35 percent; no more than about 30 percent; no more than about 25 percent; no more than about 20 percent; no more than about 18 percent; no more than about 15 percent; no more than about 12 percent, and nor more than about 10 percent. In certain embodiments, no more than about 8 percent, no more than about 7 percent; preferably no more than about 5 percent or 4 percent, more preferably no more than about 2 percent, and most preferably no more than about 1 percent of the multisubstituted polyol is formed. In certain embodiments, the functionalizing reaction results in a ratio of monosubstituted polyol to multisubstituted polyol from about 1:1 to about 50:1, preferably about 2:1 to about 40:1, and more preferably about 4:1 to about 20:1.

Typically, the final functionalized polyol mixture will comprise about 8 percent to about 50 percent of the monosubstituted polyol, preferably about 8 to about 45 percent, and more preferably about 8 to about 30 percent. The final functionalized polyol mixture will typically comprise about 1 to about 50 percent of the multisubstituted polyol, preferably about 1 to about 12 percent, and more preferably about 1 to about 5 percent. Generally, the final functionalized polyol mixture will comprise about 10 to about 91 percent of the original unsubstituted polyol, preferably about 43 to about 91 percent, more preferably about 65 to about 91 percent.

The functionalizing reaction typically comprises a nucleophilic substitution reaction or a nucleophilic addition reaction (e.g., a Michael addition reaction), wherein the nucleophile can be present on the polyol or the functionalizing reagent. For example, the reaction can involve reaction of a hydroxyl group of the polyol, or an anion thereof, as a nucleophile with a suitable electrophilic group. Alternatively, the hydroxyl groups of the polyol can be converted into good leaving groups, such as sulfonate esters, and reacted with a functionalizing reagent containing a nucleophilic group.

The functionalizing reagent will typically comprise a reactive group, X, that is either an electrophilic group reactive with a hydroxyl group or anion thereof on the polyol or, if some or all of the available hydroxyl groups of the polyol have been converted to good leaving groups, a nucleophilic group. The functionalizing reagent will also comprise the functional group, —Y, which is intended to be covalently attached to the polyol. Optionally, the functionalizing reagent will further comprise a spacer moiety linking the reactive group, X, with the functional group, —Y. Exemplary spacer moieties include —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—, —O—CH$_2$—CH$_2$—CH$_2$—CH$_2$—O—, —O—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —NH—C(O)—CH$_2$—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—, —CH$_2$—CH$_2$—C(O)—CH$_2$—CH$_2$—, —CH$_2$—C(O)—, —CH$_2$—C(O)—, —CH$_2$—CH$_2$—CH$_2$—C(O)—NH—CH$_2$—, —CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH$_2$CH$_2$)$_j$—, —NH—C(O)—O—[CH$_2$]$_h$—(OCH$_2$CH$_2$)$_j$—, bivalent cycloalkyl group, —O—, —S—, an amino acid, —N(R$^6$)—, and combinations of two or more of any of the foregoing, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —(CH$_2$CH$_2$O)$_{1-20}$—]. That is, the ethylene oxide oligomer chain can occur before or after the spacer moiety, and optionally in between any two atoms of a spacer moiety comprised of two or more atoms.

In one or more particular embodiments, the functionalizing reagent comprises the structure X-L-Y, where L is an optional linker that is interposed between X and Y. L$_0$ indicates the absence of a linker and L$_1$ indicates the presence of a linker, and L encompasses both. Preferably L is hydrolytically stable, and is made up of inert or non-reactive atoms or groups of atoms and can be any of the moieties described above with respect to the spacer moiety.

In one or more embodiments, the functionalizing reagent has the following structure:

X—(CR$_1$R$_2$)$_m$—Y         Formula IV wherein X is a group reactive with a hydroxyl group or anion thereof, or a leaving group, in a nucleophilic substitution or nucleophilic addition reaction; R$_1$ and R$_2$ are each independently selected H or alkyl; m is 0-10 (e.g., 0, 1, 2, 3, 4, 5, 6, 7, 8, 9, or 10), preferably 1-3; and Y is an ionizable functional group, optionally in protected form, and preferably selected from the group consisting of aldehyde hydrate, ketone hydrate, amine, hydrazine, hydrazide, thiol, carboxylic acid, sulfonic acid, primary amide, secondary amide, amidate, 2-substituted-1,3-oxazoline, 2-substituted 1,3-(4H)-dihydrooxazines, 2-substituted-1,3-thiazoline, 2-substituted 1,3-(4H)-dihydrothiazines, dithiopyridine, vinylpyridine, hydroxylamine, and oxime.

The X reactive group is preferably a leaving group, such as halogen (e.g., bromo or chloro) or a sulfonate ester (e.g., p-tolylsulfonyl, methylsulfonyl, trifluorosulfonyl, or trifluoroethylsulfonyl), or a substituted or unsubstituted vinyl group. The substituting group or groups attached to the vinyl group carbon atoms are typically alkyl, substituted alkyl, alkoxy, substituted alkoxy, or halogen.

In one or more embodiments, X is halogen, m is 0, and —Y is p-tolylsulfonyl, methylsulfonyl, trifluorosulfonyl, or trifluoroethylsulfonyl. Other exemplary functionalizing reagents of Formula IV include X'—(CR$_1$R$_2$)$_m$—C(O)—O—

Rp, CH$_2$=CY'—(CR$_1$R$_2$)$_m$—C(O)—O—Rp, X'—(CR$_1$R$_2$)$_m$—Z, CH$_2$=CY'—(CR$_1$R$_2$)—Z, X'—(CR$_1$R$_2$)$_m$—CN, and CH$_2$=CY'—(CR$_1$R$_2$)$_m$—CN, wherein X' is Br or Cl, Z is an ortho ester, Y' is H, halogen, alkyl, substituted alkyl, alkoxy, or substituted alkoxy, and Rp is alkyl or substituted alkyl. If the functional group, —Y, of the functionalizing reagent is in protected form, the method of the invention further comprises deprotecting the functional group. For example, if the —Y group is a protected carboxylic acid (e.g., an ortho ester or an alkyl ester), the deprotecting step comprises hydrolysis of the protecting group to form the carboxylic acid. An exemplary protected carboxylic acid group has the structure —C(O)—O—Rp, wherein Rp is an alkyl or substituted alkyl group. Protected carboxylic acids include: esters, such as methyl ester, methoxymethyl ester, methylthiomethyl ester, tetrahydropyranyl ester, benzyloxymethyl ester, phenyacyl ester, n-phthalimidomethyl ester, 2,2,2-trichloroethyl ester, 2-haloethyl ester, 2-(p-toluenesulfonyl) ethyl ester, t-butyl ester, cinnamyl ester, benzyl ester, triphenylmethyl ester, bis(o-nitrophenyl)methyl ester, 9-anthrylmethyl ester, 2-(9,10-dioxo)anthrylmethyl ester, piperonyl ester, trimethylsilyl ester, t-butyldimethylsilyl ester and S-t-butyl ester; thiolesters, such as methylthiol, ethylthiol, phenylthiol, p-snitrophenylthiol, benzylthiol and t-butylthiol; amidates such as O-alkyl-N-alkyl, O-aryl-N-alkyl, O-alkyl-N-aryl, O-aryl-N-aryl, 2-substituted-1-3-oxazolines, 2-substituted-1-3-(4H)-dihydrooxazines; thioamidates, such as S-alkyl-N-alkyl, S-aryl-N-alkyl, S-alkyl-N-aryl, S-aryl-N-aryl, 2-substituted-1,3-thiazolines, 2-substituted-1,3-(4H)-1,3-dihydrothiazines; amides and hydrazides such as N,N-dimethylamide, N-7-nitroindoylamide, hydrazide, N-phenylhydrazide, N,N'-diisopropylhydrazide.

If the —Y group is a protected amine (e.g., a carbonitrile group), the deprotecting step can comprise reducing the carbonitrile group to form the amine. Alternatively, one can consider the carbonitrile group as a protected carboxylic acid and deprotection would involve hydrolysis. Protected amines include: carbamates such as 9-fluorenylmethyl, 9-(2-sulfo)fluorenylmethyl, 9-(2,7dibromo)fluorenylmethyl, 17-tetrabenzo[a,c,g,i]fluorenylmethyl, 2-chloro-3-indenylmethyl, benz[f]inden-3-ylmethyl, 2,7-di-t-butyl-[9-(10,10-dioxo-10,10,10,10-tetrahydrothioxanthyl)]methyl, 1,1-dioxobenz[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2' and 4'-pyridyl)ethyl, 2,2-bis(4'-nitrophenyl)ethyl, N-(2-pivaloylamino)-1,1-dimethylethyl, 2-[(2-nitrophenyl)dithio]-1-phenylethyl, 2-(N,N-dicyclohexylcarboxamido)ethyl, t-butyl, 1-adamantyl, 2-adamantyl, vinyl, allyl, cinnamyl, 2-3'-pyridyl-prop-2-enyl, 8-quinolyl, N-hydroxypiperidinyl, alkyldithio, p-methoxybenzyl, p-nitrobenzyl, p-chlorobenzyl, 2,4-dichlorobenzyl, 4-methylsulfinylbenzyl, 9-anthrylmethyl, diphenylmethyl, 2-methylthioethyl, 3-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoromethyl)-6-chromonylmethyl, m-nitrophenyl, 2,5-dimethoxybenzyl, 1-methyl-1-(3,5-dimethoxyphenyl)ethyl, α-methylnitropiperonyl, o-nitrobenzyl, and 3,4-dimethoxy-6-nitrobenzyl; urea type derivatives such as phenothiazinyl-(10)-carbonyl derivative, N'-p-toluenesulfonylaminocarbonyl, N'-phenylaminothiocarbonyl; amides such as N-formyl, N-chloroacetyl, N-trichloroacetyl, N-trifluoroacetyl, N-phenylacetyl, N-3-phenylpropionyl, N-4-pentenoyl, N-picolinoyl, N-3-pyridylcarboxamido, N-benzoylphenylalanyl derivative, N-p-phenylbenzoyl, N-o-nitrophenylacetyl, N-o-nitrophenoxyacetyl, N-3-(o-nitrophenyl)propionyl, N-2-methyl-2-(o-nitrophenoxy)propionyl, N-3-methyl-3-nitrobutyryl, N-o-nitrocinnamoyl, N-o-nitrobenzoyl, N-3-(4-t-butyl-2,6-dinitrophenyl)2,2-dimethylpropionyl, N-o-(benzoyloxymethyl)benzoyl, N-2-methyl-2-(o-phenylazophenoxy)propionyl, N-4-chlorobutyryl, N-acetoacetyl, N-3-(p-hydroxyphenyl)propionyl, (N'-dithiobenzyloxycarbonylamino)acetyl, N-acetylmethionine derivative, and 4,5-diphenyl-3-oxazolin-2-one; cyclic imide derivatives such as N-phthaloyl, N-tetrachlorophthaloyl, N-4-nitrophthaloyl, N-dithiasuccinoyl, N-2,3-diphenylmaleoyl, N-2,5-dimethylpyrrolyl, N-2,5-bis(triisopropylsiloxy)pyrrolyl, N-2,5-bis(triisopropylsiloxy)pyrrolyl, N-1,1,4,4-tetramethyldisilyazacyclopenane adduct, N-1,1,3,3-tetramethyl-1,3-disilaisoindolyl, 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridonyl, 1,3,5-dioxazinyl. These and other protective groups are described in detail in Greene et al., supra.

As noted above, in one or more embodiments, the available hydroxyl groups of the polyol, or some fraction thereof, are converted to a leaving group prior to reaction with the functionalizing reagent. For example, the hydroxyl groups can be converted to a leaving group of structure –Z, wherein Z is halogen or a sulfonate ester, by reacting the polyol with a reagent having, for example, the structure X'—SO$_2$—R$_3$, wherein R$_3$ is alkyl or substituted alkyl and X' is Br or Cl. Preferred R$_3$ groups include p-tolyl, methyl, trifluoromethyl, and trifluoroethyl. In this embodiment, the conversion of the hydroxyl groups to leaving groups can serve as the controlling step used to produce the desired disparity in concentration between the monosubstituted polymer product and the multisubstituted polymer species. For instance, the reaction to convert the hydroxyl groups to leaving groups can be performed under conditions effective to form no more than about 25 percent of the multisubstituted polyol (e.g., a disubstituted polyol species having two hydroxyl groups converted to leaving groups) and typically no more than about 12 percent of the multisubstituted polyol. In certain embodiments, no more than about 8 percent, preferably no more than about 5 percent, more preferably no more than about 2 percent, and most preferably no more than about 1 percent of the multisubstituted polyol is formed. The reaction converting hydroxyl groups to leaving groups typically results in a ratio of monosubstituted polyol to multisubstituted polyol of about 1:1 to about 50:1, preferably about 2:1 to about 40:1, more preferably about 4:1 to about 20:1.

Again, in one or more embodiments, the available hydroxyl groups of the polyol, or some fraction thereof, are activated prior to reaction with the functionalizing reagent. For example, the hydroxyl groups can be activated by reacting with homo- or heterobifunctional reagents that react with the hydroxyl group to leave at the new terminus a new reactive group. Preferred non-oligomeric or polymeric homobifunctional reagents that may be used to activate the hydroxyl groups are phosgene, disuccinimidyl carbonate (DSC) and dibenzotriazoly carbonate (diBTC). Preferred non-oligomeric or polymeric heterobifunctional reagents that may be used to activate the hydroxyl groups are triphosgene and p-nitrophenyl chloroformate. In this embodiment, the conversion of the hydroxyl groups to activated groups can serve as the controlling step used to produce the desired disparity in concentration between the monosubstituted polymer product and the multisubstituted polymer species. For instance, the reaction to convert the hydroxyl groups to activated groups can be performed under conditions effective to form no more than about 25 percent of the multisubstituted polyol (e.g., a disubstituted polyol species having two hydroxyl groups converted to activated groups) and typically no more than about 12 percent of the multisubstituted polyol. In certain embodiments, no more than about 8 percent, preferably no more than about 5 percent, more preferably no more than about 2 percent, and most preferably no more than about 1 percent of the multisubstituted polyol is formed. The reaction converting hydroxyl groups to activated groups typically results in a ratio of monosubstituted polyol to multisubstituted polyol of about 1:1 to about 50:1, preferably about 2:1 to about 40:1, more preferably about 4:1 to about 20:1.

D. Purification Step

The process of functionalizing a polyol starting material results in a mixture of products, including a monosubstituted polyol and one or more multisubstituted polyol species (e.g., a disubstituted polyol). Thus, in order to make the method of invention of the utmost practical utility, the product polyol mixture is preferably purified to separate the monosubstituted polyol from the di- or multi-substituted polyol, as well as any remaining unreacted polyol or other neutral polymer species. Any of a number of purification techniques suitable for separating species based on charge can be used.

In a preferred embodiment of the invention, ion exchange chromatography is employed to separate the various polyol constituents of the product mixture based on their differences in charge. In one aspect, the present invention provides an ion exchange chromatography approach that overcomes the problems associated with other commonly employed ion exchange methods, such as gradient elution chromatography, although any ion exchange method, including gradient methods, can be used without departing from the invention. However, gradient-based methods are less preferred.

Gradient-based chromatography involves changing the ionic strength of the mobile phase or eluent to drive differently charged molecules off an ion exchange column at different intervals. Generally, in a gradient chromatography, a gradient is applied that changes from a poor or low eluting strength solvent to a good or high eluting strength solvent, based upon the relative affinity of the column versus the mobile phase for a particular polyol.

In a typical gradient separation, a sample is applied to a column and a low eluting strength solvent is employed, so as not to allow any separation to occur initially. Rather, the mixture components are collected at the top of the column, in a concentrating step. The gradient is then progressed and the ionic strength of the solvent is gradually increased until "good" or high eluting strength solvent conditions are achieved such that sample components begin their separation and begin to migrate. Charged substances are separated via column materials carrying an opposite charge. Species with a higher charge are bound to an ion exchange column more strongly, while the less highly charged species elute more rapidly. The strength of the eluent is typically altered by changing pH, buffer, and/or salt concentration (ionic strength). Techniques that rely upon gradient separation are tedious, time-consuming, use large volumes of solvent, and require analysis of multiple fractions. Thus, gradient type methods are poorly suited for commercial-scale processes. Moreover, gradient-based separation techniques also rarely achieve relatively high purity levels of any given polyol (e.g., in reference to the number of various polyol species present and the polydispersity of the purified polyol product), particularly when separating higher molecular weight polyol species such as those species that may result from functionalizing an ethoxylated polyol starting material mixture.

A preferred method for carrying out the purification step involves ion exchange chromatography, the method preferably not including the use of gradient-based chromatography. The preferred ion exchange chromatography method used in the purification step is well suited for polyol mixtures that contain uncharged and charged substances differing in charge, e.g., polyols that are uncharged, singly charged, doubly charged, triply charged, and so on (that is, two or more species having ionizable groups that under certain pH conditions, carry different charges). One such example is a polyol mixture containing a neutral polyol (i.e., a polyol absent an ionizable functional group), a monosubstituted polyol having a single ionizable group, such as an amine or carboxylic acid group, and a di- or multi-substituted polyol having two or more ionizable functional groups. Separation is achieved by relying upon differences in charge, and, in certain embodiments, differences in molecular weight. Rather than eluting species having different charges from a single column (or a number of single column chromatograph separations) by changing the ionic strength of the eluate in a stepwise, gradient fashion, the ion exchange method involves the use of discrete columns and discrete eluates. Generally, a solvent having a constant or static concentration as it is fed into a column is used. That is to say, the solvent feed as is enters the column is of a constant, non-gradient composition. The ionic strength and/or pH of the solvent is adjusted to suit the polyol species being eluted from the column.

Preferably, the ion exchange method used in the purification step involves the use of more than one ion exchange column to achieve ultra high purity mono-substituted polyols, e.g., typically containing less than 0.3% by weight difunctionalized or multi-functionalized polyol impurities.

The first column(s) or pre-column(s) are sized to adsorb substantially all, and most preferably, all, of the disubstituted polyol and other multisubstituted polyol species that are present in a polyol mixture. Typically, determination of an appropriate size for the first column(s) or pre-column(s) involves the step of establishing column capacity. Column capacity is experimentally determined and typically involves passing a solution containing an excess amount of standard solution of one type of species of polyol known to adsorb to the stationary phase. This standard is added so as to saturate the column, often verified by detecting the polyol species in the eluate retrieved from the column. Thereafter, any nonadsorbed species are washed out of the column, typically by passing distilled water through the column. Next, all polyol species adsorbed on the column are eluted (generally by means of passing a salt solution), extracted with organic solvent and then weighed after removal of solvent. This amount corresponds to the column capacity. To the extent that two or more columns are provided in series, the overall column capacity of the system is equivalent to the added column capacities of the individual columns.

Having established column capacity, only column(s) sufficiently sized to adsorb substantially all of the di- or multi-substituted polyol species (e.g., disubstituted polyol, polyol species comprising two $-L_{0,1}-Y$ groups, or difunctional polyol) desired to be removed form a mixture will be used in an initial purification step. A column is sufficiently sized in this regard when it has a column capacity greater than the amount of the di- or multisubstituted polyol species to be retained from a mixture. As discussed previously, the amount of the polyol species in any mixture can be determined by analyzing a sample of the mixture, by having reference to FIG. 1., or any other art-known method.

Thus, the column capacity of pre-column(s) used in a first eluting step can be one or more of at least a 10%, at least a 20%, at least a 30%, at least a 40%, at least a 50%, at least a 60%, at least a 70%, at least a 80%, at least a 90%, at least a 100%, and at least a 110% increase of the total amount of the polyol species in the mixture to be purified. For example, with respect to a first step in a method for purifying of a mixture containing 5 g of disubstituted polyol, a first ion exchange column having capacity to adsorb 10 g of the disubstituted polyol can be used (thereby representing 100% increase of the total amount of the difunctional polyol species to be adsorbed on the first column). In addition, a mixture containing 25 g of disubstituted polyol, a first ion exchange column having capacity to adsorb 35 g of the disubstituted polyol can be used (thereby representing a 40% increase of the total amount of the polyol species to be adsorbed on the first column).

With respect to the second column(s) or main column(s) used in the purification step, it is sufficient to have a column capacity substantially equivalent to the amount of monofunctional polyol within the polyol species to be retained from the mixture (e.g., monosubstituted polyol, polyol species comprising one -$L_{0,1}$-Y groups, or monofunctional polyol). Second or main column(s) having greater column capacities can also be used to prevent any losses of monofunctional polyol(s).

Having identified appropriate columns, purification can take place. Advantageously, the polyol mixture equilibrates with the solid phase media in the precolumn as the mixture flows through the column to allow the strongest binding material (e.g., those species bearing the greatest number of the charges to which the column is directed) to be retained. Slower rates of adding the mixture correspond to an increased extent of equilibration.

In one or more embodiments, a plurality of "precolumns" (e.g., 2, 3, or 4 precolumns) connected in series is used to remove the multisubstituted polyol species, the plurality of precolumns being sized to collectively adsorb all of the disubstituted polyol and other multisubstituted polyol species. Typically, some amount of monosubstituted polyol species will be adsorbed as well, but to a lesser extent since only one ionized species is associated with the monosubstituted polyol species.

Advantageously, the purification method does not require the use of a distillation step to concentrate solutions such as the eluate. Furthermore, the purification method described herein is suited to purify not only relative small molecular weight polyols (e.g., 1,000 Da), but can be used to purify molecules with polyol cores having higher molecular weights as well. Thus, the purification method is suited for purifying molecular weights in the following ranges: from about 44 Da to about 180,000 Da; from about 3,000 Da to about 120,000 Da; from about 5,000 Da to about 100,000 Da; from about 8,000 Da to about 100,000 Da; from about 10,000 Da to about 100,000 Da; from about 12,000 Da to about 80,000; and from about 15,000 Da to about 80,000 Da. In addition, the equipment used in the purification process does not rely on gradients, thereby reducing the need for obtaining many very diluted eluate fractions, which, in turn, requires a multitude of collection vessels. Furthermore, the present method uses substantially less volumes of eluent compared to gradient-based methods, typically on the order of less than about 50% eluent, preferably less than about 75% eluent, more preferably less than about 85% eluent, still more preferably less than about 90% eluent, with eluent amounts of less than about 95% relative to prior art methods being most preferred. Consequently, the methods described herein require only a single collection vessel, and do not require a distillation step to concentrate eluate to enable extraction of purified product. In addition, the apparatuses described herein do not require more than a single collection vessel and do not require a means for distillation.

The eluate from the first column, which contains the monosubstituted polyol and the neutral polyol, is then passed through the second (or main) ion exchange column or columns connected in series. The monosubstituted polyol is absorbed onto the second (or main) column(s), which are sized in order to retain preferably all of the monosubstituted polyol. The neutral polyol passes through all of the columns and can be collected and possibly recycled for reuse. It is generally preferred to wash each column with a solution having low ionic strength (e.g., deionized water) to remove any remaining neutral polyol thereon.

Solutions having the requisite low ionic strength for any particular system are known to those having ordinary skill in the art. In addition, solutions having the requisite low ionic strength can be determined through routine experimentation by passing a candidate solution (typically, although not necessarily, a very weak salt solution or buffered solution) through column(s) known to have both charged and neutral polyol species contained therein, collecting the candidate solution that has passed through the column(s), and then testing the collected solution for the presence of any charged polyol species. A candidate solution having passed through the column(s) with no or substantially no (e.g., less than 1%) charged polyol species content represents a solution having a low ionic strength for that particular system.

Retrieval of charged polyol species (whether they be singly charged polyol species or di- or multiply charged polyol species) adsorbed onto the ion exchange columns typically requires desorbing. Desorption typically involves passing salt solution having high ionic strength through the column(s), thereby desorbing charged polyol species. For instance, the second (or main) column(s) containing monosubstituted polyol can be washed with a salt solution having high ionic strength, such as a NaCl solution, to remove and collect a substantially pure monosubstituted polyol product.

Salt solutions having the requisite high ionic strength for any particular system are known to those having ordinary skill in the art. In addition, solutions having the requisite high ionic strength can be determined through routine experimentation by passing a candidate solution through the column(s) having a known amount of charged polyol species adsorbed therein, collecting the candidate solution that has passed through the column(s), and then testing the collected solution for the presence of charged polyol species. A candidate solution having passed through the column(s) with at least about 85%, more preferably at least about 90%, still more preferably at least about 95%, and most preferably at least about 99% of the known amount of charged polyol species contained therein represents a solution having a high ionic strength for that particular system. This procedure can be used to identify a solution having sufficient ionic strength so that the solution will desorb difunctional polyol through the first column or precolumn.

Since the differently charged polyol species have been separated by adsorption on separate columns, there is no need to use a salt solution gradient to recover each polyol species separately. Instead, a salt solution having a constant ionic strength can be used to elute the desired product from each column.

If desired, the multisubstituted polyol species absorbed on the precolumn(s) can also be collected by passing a salt solution through the precolumn to drive desorption of the polymer. Typically, the precolumn(s) are sized so as to ensure absorption of all of the multisubstituted polyol in the feed stream, meaning that some monosubstituted polyol will also be absorbed on the precolumn. Thus, purity of the multisubstituted product eluate is typically lower as compared to the monosubstituted product eluted from the one or more main columns. Preferably, the product eluted from the precolumn(s) contain no more than about 70 weight percent monosubstituted polyol, more preferably no more than about 50 weight percent, and most preferably no more than about 30 weight percent. If the product eluted from the precolumn(s) contain multiple multicharged polyol species (e.g., doubly-charged and triply-charged), then a second pass through the ion exchange system can be used to further separate the polyol mixture by retaining the higher charged species in the precolumns (e.g., the triply-charged species) and retaining the less highly charged species (e.g., doubly-charged) in the second column.

Analytical determination, using an HPLC column that responds to both charge and molecular weight, can be used to determine how much of each species is present in a sample, both before being run through a column and after. By "substantially pure" is meant that the monosubstituted polyol contains less than about 5 weight percent polyol impurities, such as multisubstituted polyol or unsubstituted (i.e., neutral) polyol, preferably less than about 3 weight percent, more preferably less than about 2 weight percent, and most preferably less than about 1 weight percent.

Where the polyol mixture to be purified is an ethoxylated polyol mixture or a mixture of polyols containing other types of water soluble and non-peptidic polymer segments, it may be desired to narrow the molecular weight range (i.e., polydispersity) of the monosubstituted polyol product. A series of two or more columns (e.g., 2, 3, 4, 5, 6, 7, 8, 9, or columns) following the precolumn can be used to attenuate the molecular weight range of the monosubstituted polyol absorbed on each column. Monosubstituted polyol of smaller molecular weight will absorb first, meaning the average molecular weight of the polyol material absorbed on each successive column will increase. Thus, by increasing the number of columns, one can not only separate the monosubstituted polyol from the higher charged species, but also lower polydispersity. In certain embodiments, the polydispersity of the monosubstituted polyol is reduced by at least about, 0.01 preferably at least about 0.02, more preferably at least about 0.03, and most preferably at least about 0.05. In an alternative embodiment, if lower molecular weight monosubstituted polyol is the desired product, one can simply undersize the second or main column such that all of the monosubstituted polyol cannot be adsorbed thereon. Since lower molecular weight species will selectively bind first, the desired lower molecular weight monosubstituted polyol will absorb on the column. In addition or alternatively, one can use several columns and collect lower molecular weight monofunctional polyol from the first column in the series of columns following the precolumn.

Following purification, if desired, the substantially pure monosubstituted polyol can be further modified to convert the ionizable functional group to a second functional group, such as hydroxyl, active ester, active carbonate, ortho ester, acetal, aldehyde, aldehyde hydrates, ketone, ketone hydrate, alkenyl, acrylate, methacrylate, nitrile, primary or secondary amide, imide, acrylamide, active sulfone, amine, hydrazide, thiol, carboxylic acid, isocyanate, isothiocyanate, maleimide, substituted succinimide, vinylsulfone, dithiopyridine, vinylpyridine, amidate, 2-substituted-1,3-oxazoline, 2-substituted 1,3-(4H)-dihydrooxazines, 2-substituted-1,3-thiazoline, 2-substituted 1,3-(4H)-dihydrothiazines, hydroxylamine, iodoacetamide, epoxide, glyoxal, dione, mesylate, tosylate, and tresylate. Where the polyol does not yet contain polymeric arms of the desired lengths, the step of converting the ionizable functional group can occur before or after attachment of the polymeric segments to the purified polyol core. If desired, the ionizable functional group can be converted to a functional group adapted for reaction with a polymeric segment such that a water soluble and non-peptidic polymer segment is attached at the site of the ionizable functional group as well as the site of the available hydroxyl groups of the polyol.

During the ion exchange process, the eluate from each column can be monitored using techniques known in the art, such as by measuring the conductivity of the eluate, analyzing the eluate by ion exchange chromatography, size exclusion chromatography, high performance liquid chromatography, or thin layer chromatography, or where PEG segments are present in the polyol mixture, by detecting the presence of PEG in the eluate by treating a drop of eluate with a drop of 1% polyacrylic acid (Aldrich, Mn 250,000) in 1 N HCl ("PAA test"). Presence of PEG is indicated by the immediate appearance of a white precipitate of PEO/PAA complex. This test is very specific to the polyether backbone of PEG and not influenced by end group modifications of the polymer, molecular weight, or the presence of inorganic ions in the analyzed solution. Monitoring of the eluate streams is particularly important during the washing step to determine when substantially all the neutral polyol has been removed from the columns.

The ion exchange columns utilized in the present invention can be any ion exchange columns conventionally used to separate a mixture based on charge (Ion Exchange Chromatography. Principles and Method. Pharmacia Biotech 1994; "Chromatography: a laboratory handbook of chromatographic and electrophoretic techniques." Heftman, E (Ed.), Van Nostrand Rheinhold Co., New York, 1975). Each column comprises an ion exchange media and a mobile phase or eluent that passes through the ion exchange media. Ion exchange columns suitable for use in the present invention include POROS® ion exchange media made by Applied Biosystems and SEPHAROSE® ion exchange media made by Pharmacia.

The ion exchange media, which is typically a polymeric resin (e.g., dextran, agarose, cellulose, styrene-divinylbenzene copolymer) containing charged groups, is selected based on a number of factors, including the charge and pKa value of the ionizable functional group present on the polyols to be separated. Typically, the ion exchange media is selected so as to provide a sufficient difference in pKa value between the ionizable functional group and the ion exchange media to favorably drive absorption of the polyol, preferably a difference of at least 4-5 units. The ion exchange media will comprise negatively charged groups (i.e., a cation exchanger) if the ionizable functional group is positively charged and will comprise positively charged groups (i.e., an anion exchanger) if the ionizable functional group is negatively charged. Exemplary negatively charged groups that may be used include carboxymethyl (CM), sulphopropyl (SP), and methyl sulphonate (S). Exemplary positively charged groups include triethylammoniumethyl (TMAE), diethylaminoethyl (DEAE), quaternary aminoethyl (QAE), and quaternary ammonium (Q). Typically, the media in each column will be the same, but different media could be used in each column without departing from the present invention.

A two column embodiment of the ion exchange system useful in the practice of the methods described herein is shown in FIG. 1. As shown, the ion exchange system 10 comprises a feed tank or vessel 12 that contains a supply of the solution of the crude polyol mixture to be separated. Typically, the polyol mixture will be dissolved in deionized water or a neutral aqueous solution having very low ionic strength. As noted above, the polyol mixture will often include a neutral or unsubstituted polyol species, a monosubstituted polyol, and a multisubstituted polyol (such as a disubstituted polyol).

The feed tank 12 is in fluid communication with a first ion exchange column or precolumn 16 sized to trap higher charged species (e.g., a disubstituted polyol). The outlet of the precolumn 16 is in fluid communication with the inlet of the second or main ion exchange column 18, which is appropriately sized to retain all of the monocharged polyol species. The outlet of each column is in fluid communication with one or more product recovery or receiving vessel 20, each vessel adapted to receive eluate from one or more of the columns. The salt solutions and neutral solutions used to wash the columns and/or recover the absorbed polyol species can be housed in one or more solvent vessels 22, which are in fluid communication with the inlet of one or more of the columns.

FIG. 2 illustrates an embodiment comprising a precolumn 16 and a plurality of second or main columns 18 that can be used to narrow the molecular weight range of the desired monosubstituted polyol product as explained above. Purification methods and apparatus that may be used to carry out the purification step are also described in U.S. 2005/0054816 to McManus et al., which is incorporated by reference herein.

The above-noted purification process can be applied at various stages in the process of the invention, such as before or after attachment of water-soluble polymer segments. Following purification according to the present invention, branched polyols and multiarm polymers can exhibit a purity of at least about 83%, more preferably at least about 91%, still more preferably at least 95%, yet still more preferably at least 96%, still more preferably at least 97%, yet still more preferably at least 98%, still more preferably at least 99%, and in some cases about 100% purity. As used herein, purity for a given composition refers to the percentage of polymeric species in the composition having the same branched or multiarm arrangement and the same number and type of termini (wherein variations in molecular weight within one standard deviation of the average are not considered to affect purity).

E. Exemplary Reaction Schemes

To further illustrate certain embodiments of various aspects of the invention, exemplary reaction schemes are provided below. These schemes are meant to be representative. The schemes provided below can be extended to any of the polyols, polymers, functionalizing reagents, leaving groups, protecting groups, and purification modes described herein.

Scheme 2 below illustrates one way that functionalization may be carried out to provide control over how many functional groups are attached. In this example, blocking or protecting groups are added to the core molecule to provide a limited number of sites for attachment. In this example, two sites are left open for attachment. The functional group in this example is added as a blocked or protected group (a protected carboxylic acid). As functionalization of the diol will proceed in a statistically predictable manner to provide a mixture of diol, monofunctionalized product, and difunctionalized product, the stoichiometry of the reaction can be set to provide the maximum amount of monofunctionalization.

Turning now to the specifics of the reaction shown in Scheme 2, dipentaerythritol available from Aldrich is reacted with benzaldehyde to create a cyclic acetal group on each end of the polyol, thereby protecting four total hydroxyl groups of the polyol and leaving two available for functionalization. Thereafter, a functionalizing reagent carrying a carboxylic acid group protected in the form of an ortho ester is reacted with the polyol, which results in a mixture of products comprising an unsubstituted diol (i.e., the unreacted polyol with two available hydroxyl groups), a monosubstituted polyol comprising a single ortho ester group attached thereto, and a disubstituted polyol comprising two ortho ester groups attached thereto. Acid-catalyzed hydrolysis is utilized to deprotect the carboxylic acid groups and the mixture is then purified using ion exchange chromatography to yield purified fractions of the species of the mixture.

The progress of the functionalizing reaction can be monitored to ensure the reaction is stopped or quenched at the desired time, although using a known amount of starting materials and a limited amount of the functionalizing reagent will stop the reaction automatically as a result of exhaustion of the functionalizing reagent. Again, routine experimentation will provide the amount of functionalizing reagent that will result in the desired amounts of products. The progress of the reaction can be monitored using any one of a number of analytical techniques, such as $^1$H NMR or HPLC.

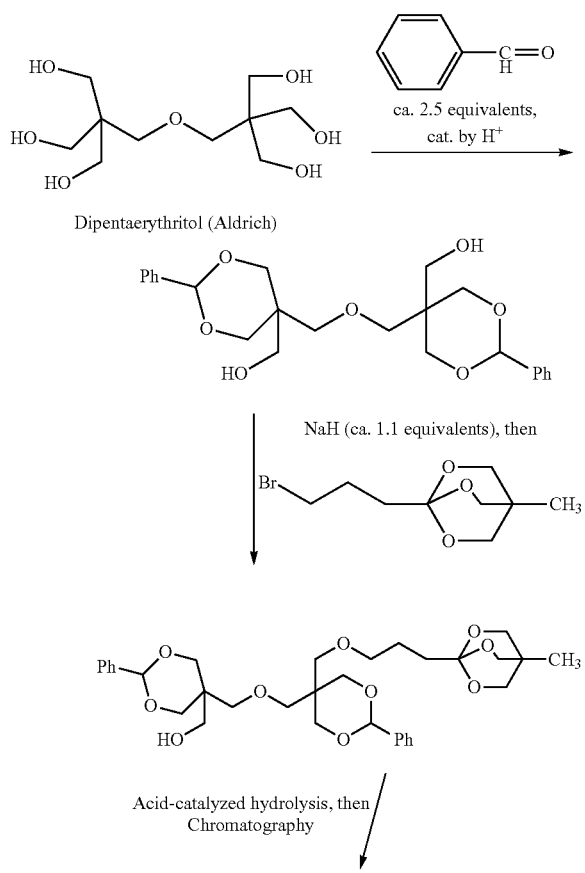

Scheme 2

-continued

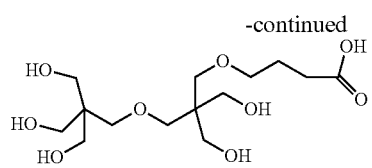

plus other fractions including
dicarboxylic acid and neutral species

The purified polyol product of Scheme 2 can be further manipulated as desired. For example, the polyol can be functionalized with polymer segments, which in turn can be functionalized as necessary for binding with drug molecules or other biologically active agents.

Scheme 3 below shows additional processes that can be carried out on the purified polyol carboxylic acid of Scheme 2. In the top reaction of Scheme 3, the carboxylic acid is esterified. Thereafter, the polyol can be converted to a poly (succinimidyl carbonate), which can then be reacted further to elaborate the molecule. The second reaction in Scheme 3 shows how one can ethoxylate the purified polyol to produce a polymeric polyol that retains the carboxylic acid functional group as such a group is incapable of being ethoxylated under typical conditions. As noted previously, the ethoxylation could be conducted prior to purification if it is desired to purify the product mixture at a later stage. Following ethoxylation and optional ion exchange chromatography, as shown in Scheme 3, the carboxylic acid group is reduced to form a six-armed polyol that is then ready to be activated and reacted with a drug molecule.

Scheme 3

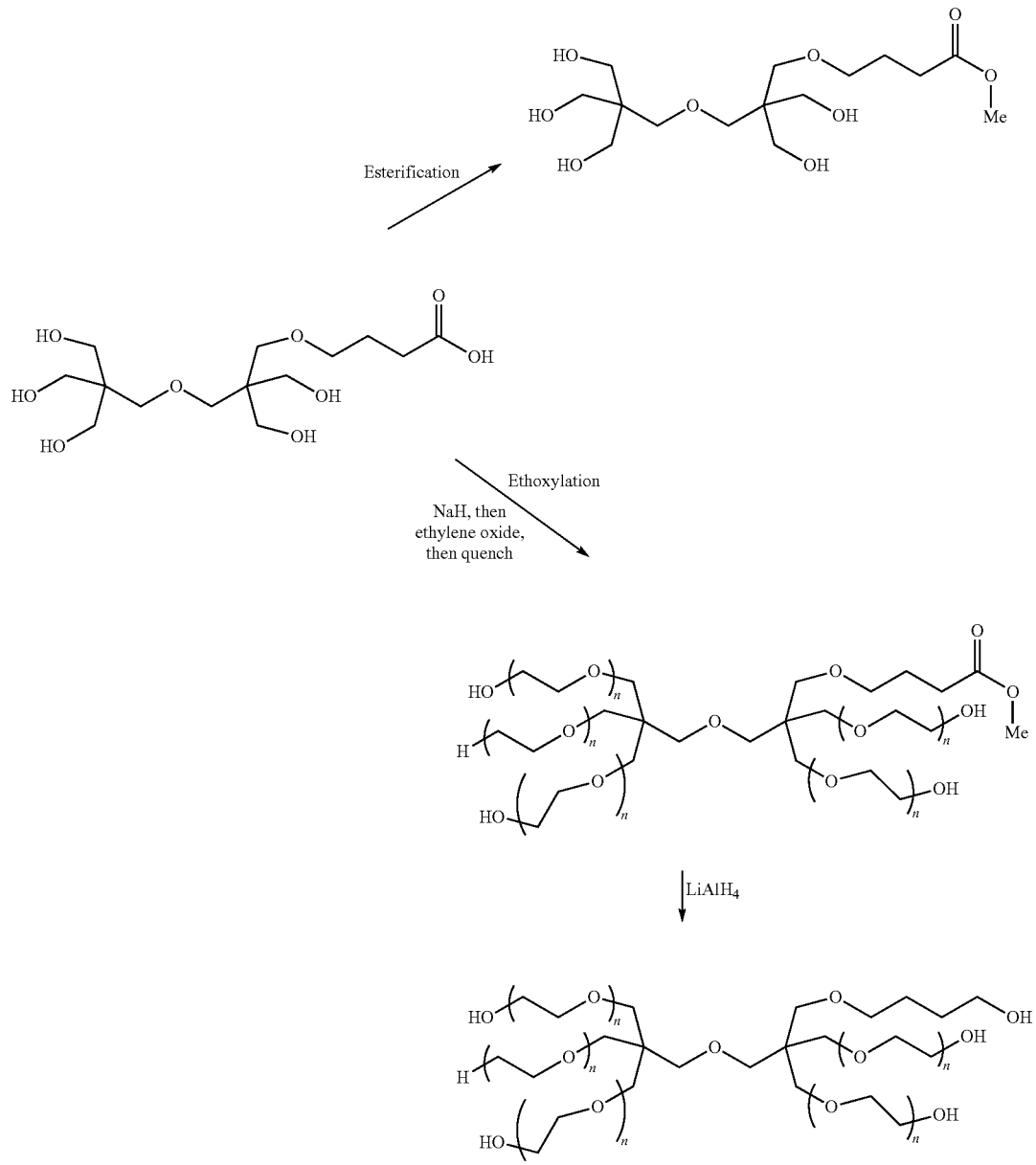

In some embodiments it may be desirable to carry out purification prior to deprotection. This is illustrated in Scheme 4 below. In Scheme 4, tripentaerythritol is reacted with cyclohexanone to protect 6 of the 8 hydroxyl groups in the form of a cyclic ketal group. The resulting diol is reacted with α-bromoacetate. Since the reaction with the α-bromoacetate occurs, according to chance, at neither hydroxyl group, one hydroxyl, or both hydroxyls, with about 1 equivalent of the α-bromoacetate, the resulting mixture will be about 1:2:1 unreacted starting material:monosubstituted ester:disubstituted ester. Chromatography following hydrolysis of the ester to carboxylic acid separates these products to give the monosubstituted carboxylic acid free of unreacted starting material, which can be recycled, and dicarboxylic acid.

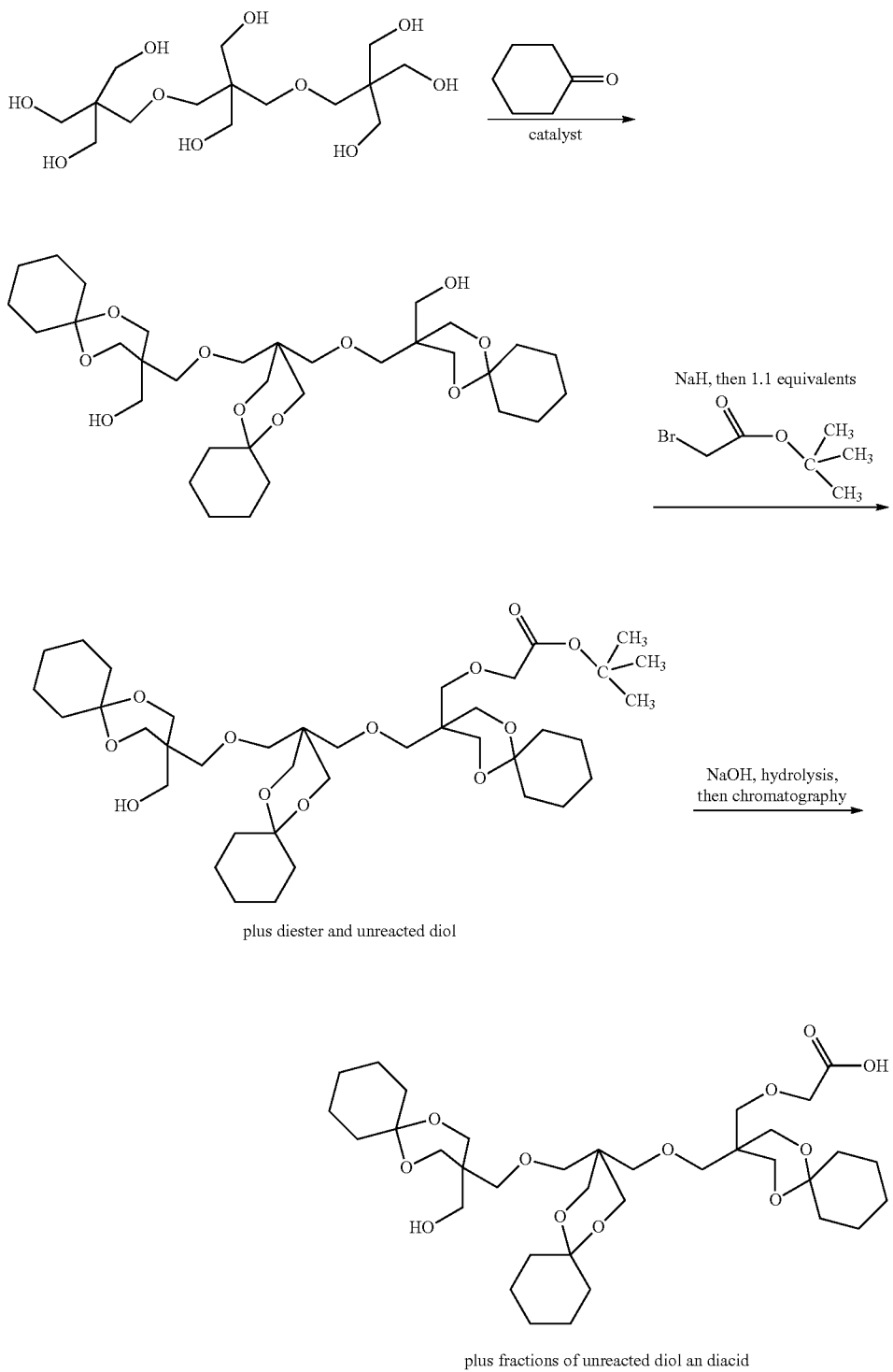

The final series of schemes illustrate how pentaerythritol is converted into a protected form. Note that the protection step and ethoxylation step is combined into a single step by using a monoprotected PEG, in this case a triethylene glycol derivative. The preferred base in the first reaction is sodium hydride, which may be used in a ratio to prefer the desired amount of substitution. For convenience, only one product form is shown in Scheme 5. However, use of an excess of the protecting agent, a trityl protected triethylene glycol chloride, will give predominantly a single product because steric hindrance significantly slows the reaction as more than two groups are added and addition of a fourth is very difficult.

Scheme 5

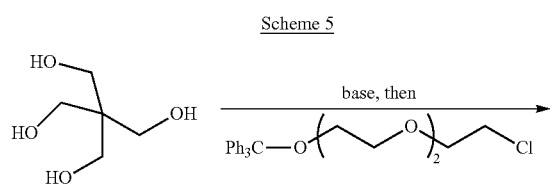

In Scheme 6 below, the protected pentaerythritol is reacted with an excess of disuccinimidyl carbonate (DSC) in the presence of a basic catalyst to give an active intermediate. This reactive intermediate is then treated with an excess of lysine to give substitution on each of the lysine amine groups and leaving the carboxylic acid group to make the purification step effective. During chromatography of this derivative, several anticipated side products from the previous steps will be removed. For example, in the formation of the trityl protected pentaerthritol derivative, mono-, di- and tetratritylated forms will have either have reacted with lysine to form dicarboxylic acid (di) or tricarboxylic acid (mono) or, it will not reacted to form acid (tetra). All of these impurities would be removed by chromatography. Also, if incomplete reaction with lysine occurs, the products would have unreacted amine groups which would give the polymer chromatographic properties different from the desired acid and they would be separated.

Scheme 6

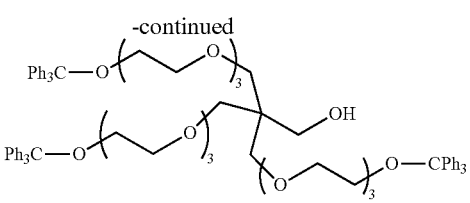

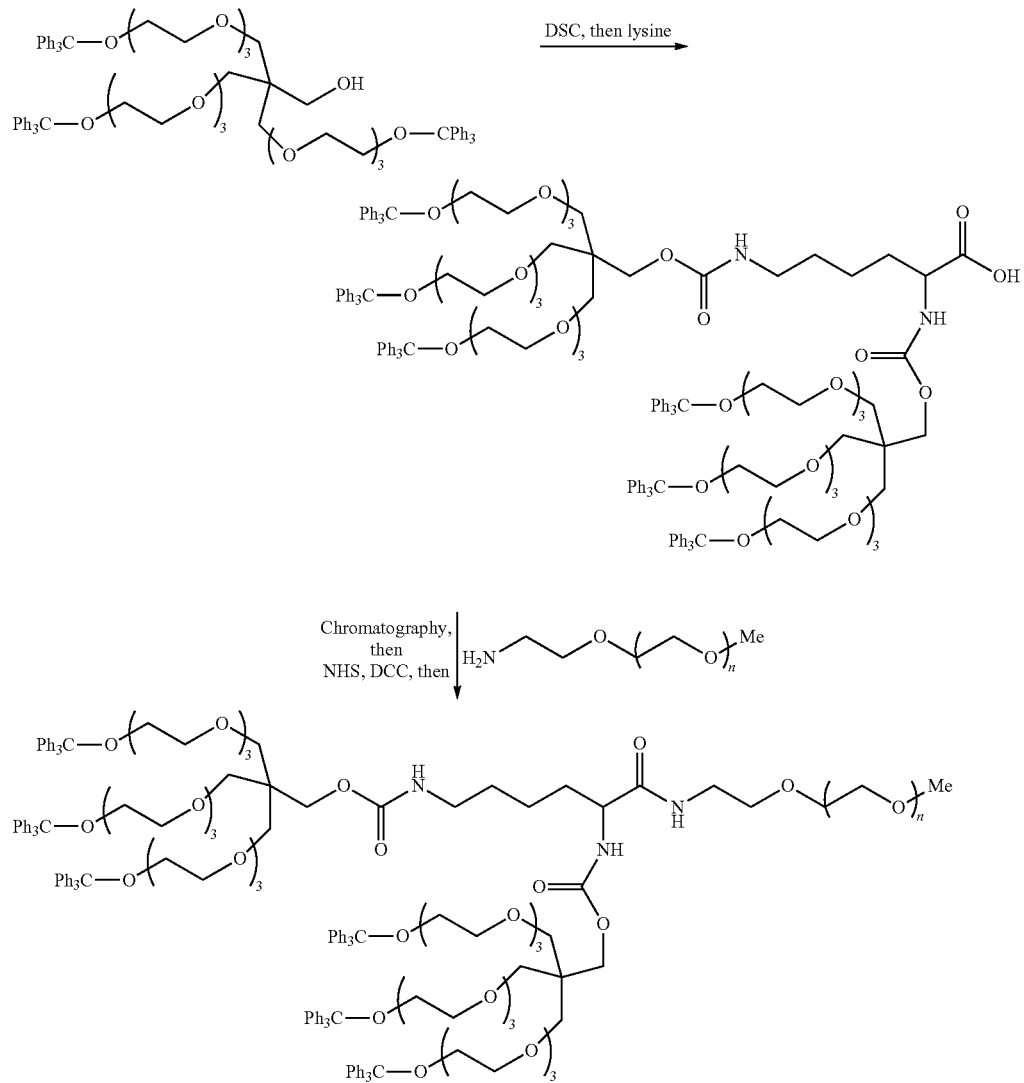

The next step, Scheme 7, is a deprotection step. The trityl groups are removed to give the purified polymeric polyol.

Scheme 7

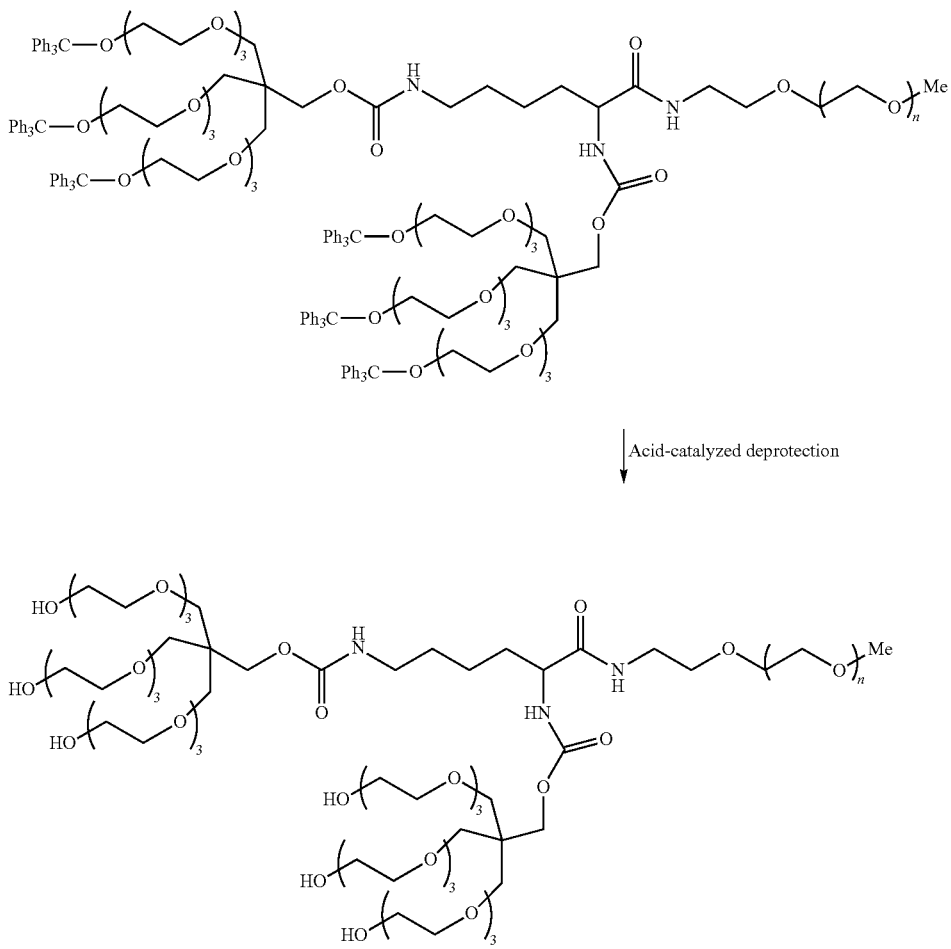

The resulting polyol of Scheme 7 can be converted into an activated form for attachment of drug molecules. The desired activated functional group will depend on the particular application, such as the structure and available functional groups of the drug to be conjugated. Numerous activation reactions could be utilized and any of the functional groups described herein could be attached to the termini of the polyol of Scheme 7.

All articles, books, patents, patent publications and other publications referenced herein are hereby incorporated by reference in their entireties.

EXPERIMENTAL

It is to be understood that while the invention has been described in conjunction with certain preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains.

All PEG reagents referred to in the appended examples are commercially available unless otherwise indicated, e.g., from Nektar Therapeutics, Huntsville, Ala. All $^1$HNMR data was generated by a 300 or 400 MHz NMR spectrometer manufactured by Bruker. High Performance Liquid Chromatography (HPLC) was performed using Agilent 1100 HPLC system (Agilent), gel permeation or ion exchange column, aqueous phosphate buffer as a mobile phase, and refractive index (RI) detector.

Example 1 illustrates a method of forming a 3-arm PEG having a butanoic acid group as the ionizable group for purification purposes. As shown, a protected carboxylic acid containing reagent is reacted with the starting polyol material using a controlled amount of reagent in order to minimize multiple substitution of the protected carboxylic acid onto the polyol. Thereafter, the protected carboxylic group is deprotected and the polyol is purified by chromatography. The resulting purified product is then modified to protect the carboxylic acid, the hydroxyl groups are activated, and polymer segments are attached. The carboxylic acid is once more deprotected and a second chromatographic purification step is utilized to form the final product.

In Example 2, a protected carboxylic acid-containing group is attached to a polyol and thereafter hydroxyl groups are activated and polymer segments are attached without an intervening purification step. The protected carboxylic acid is then deprotected and chromatography is used to purify the final product. FIG. 4 is a GPC chromatograph of the product of Example 2. As shown, the chromatograph shows a single peak, indicating a highly pure product. By comparison, FIG. 3, which is a GPC chromatograph of a commercially available multiarm PEG molecule, shows four distinct peaks. Peak 1 is a high molecular weight impurity, Peak 2 is the main product, and Peaks 3 and 4 are low molecular weight impurities.

Example 1

3ARM-PEG (15 KDa)-mono-butanoic acid

A. Pentaerythritol ethoxylate-mono-butanoic acid

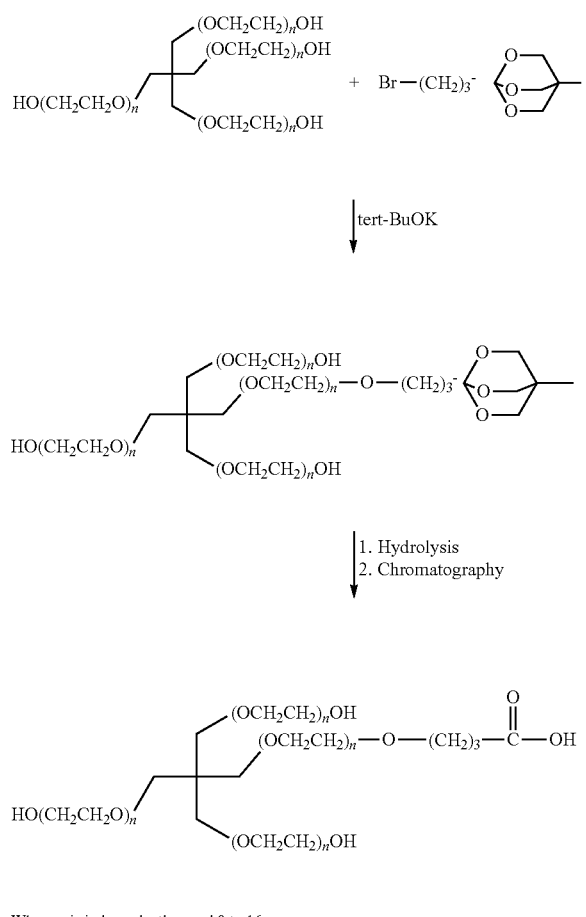

Where n is independently equal 0 to 16

A solution of pentaerythritol ethoxylate (15/4 EO/OH) (100 g, 0.5019 OH equivalents), in toluene (200 ml) was azeotropically dried by distilling off toluene under reduced pressure. The dried pentaerythritol ethoxylate was dissolved in anhydrous toluene (180 ml) and a 1.0 M solution of potassium tert-butoxide in tert-butanol (120 ml, 0.120 moles) and 1-(3-bromopropyl)-4-methyl-3,6,7-trioxabicyclo[2,2,2]octane (26.0 g, 0.104 mole) were added. Next, the mixture was stirred at 80° C. overnight under an argon atmosphere. After cooling to room temperature, the mixture was filtered and the solvents were distilled off under reduced pressure. The crude product was dissolved in 300 ml deionized water. The pH of the solution was adjusted to 2 with 5-% phosphoric acid and the solution was stirred 15 minutes at room temperature. Next the pH was readjusted to 12 with 1M sodium hydroxide and the solution was stirred 1.5 hours while maintaining the pH equal to 12 by periodic addition of 1M sodium hydroxide solution. NaCl (15 g) was added and the pH of the solution was adjusted to 3 with 5% phosphoric acid. The product was extracted with dichloromethane (250, 150, and 150 ml). The extract was dried with anhydrous magnesium sulfate and the solvent was distilled off. Yield 64.7 g.

NMR ($d_6$-DMSO): 1.71 ppm (q, $\underline{CH_2}$—$CH_2$—COO—) 2.24 ppm (t, —$CH_2$—COO—), 3.25 ppm (s, —C—$CH_2$—O—), 3.51 ppm (s, PEG backbone).

Anion exchange chromatography showed that the product contained: pentaerythritol ethoxylate tri-butanoic acid 0.1%, pentaerythritol ethoxylate di-butanoic acid 6.6%, pentaerythritol ethoxylate mono-butanoic acid 42.3% and pentaerythritol ethoxylate 51.0%.

The crude product was dissolved in distilled water (3500 ml) and the obtained solution was filtered though a precolumn filled with DEAE Sepharose FF anion exchanger (320 ml) which removed certain undesired components of the mixture. Anion exchange chromatography analysis showed that the eluted solution contained only pentaerythritol ethoxylate mono-butanoic acid 54.8% and pentaerythritol ethoxylate 45.2%. Next the solution was applied onto a main column filled with DEAE Sepharose FF (1000 ml) and the column was washed with 2200 ml of distilled water. The product, which had adsorbed on the column, was eluted with 10% NaCl solution (1800 ml). The pH of the eluate was adjusted to 3 with 5% phosphoric acid and the product was extracted with dichloromethane. The extract was dried with anhydrous magnesium sulfate and the solvent was distilled off. Yield 27.6 g.

Anion exchange chromatography showed that the eluted product contained only peak, that owing to pentaerythritol ethoxylate mono-butanoic acid, which was 100% pure by this analysis, meaning it is believed that the product is monodisperse (i.e., comprises a single polyol specie).

B. Pentaerythritol ethoxylate-mono-butanoic acid, methyl ester

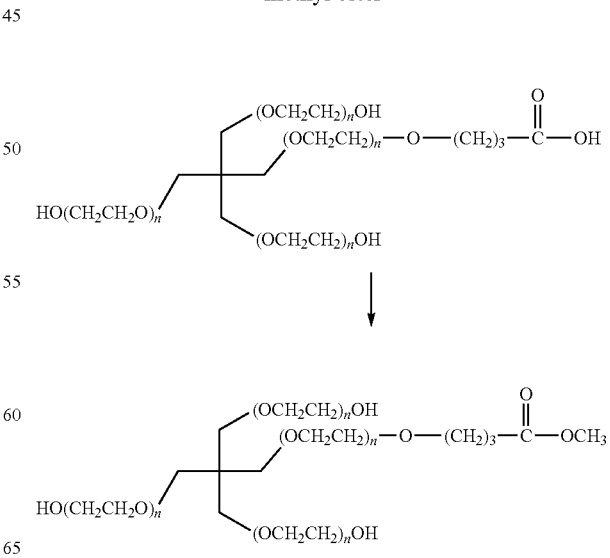

Pentaerythritol ethoxylate-mono-butanoic acid (12 g) was dissolved in anhydrous methanol (130 ml) and concentrated $H_2SO_4$ (1.7 ml) was added. The solution was stirred 4 hours at room temperature. $NaHCO_3$ (8% aqueous solution) was added to adjust the pH of the mixture to 6.5 and the solvents were distilled off under reduced pressure. The residue was extracted with methanol (250 ml×3). The combined methanol extracts were dried with $MgSO_4$. After filtration, the methanol was distilled off under reduced pressure giving 10.4 of liquid product.

NMR ($D_2O$): 1.82 ppm (q, CH$_2$—CH$_2$—COO—), 2.39 ppm (t, —CH$_2$—COO—), 3.33 ppm (s, —C—CH$_2$—O—), 3.63 ppm (s, PEG backbone).

C. Pentaerythritol ethoxylate-mono-butanoic acid, methyl ester, tri-succinimidyl carbonate

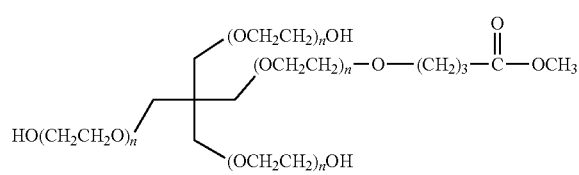

Pentaerythritol ethoxylate-mono-butanoic acid, methyl ester (2.0 g. 0.006226 —OH equivalents) was dissolved in acetonitrile (25 ml) and anhydrous pyridine (0.70 ml) and disuccinimidyl carbonate (1.75 g, 0.006831 moles) were added to the solution. The mixture was stirred overnight at room temperature under an argon atmosphere. The resulting solution was used directly in the next synthetic step.

NMR ($CDCl_3$): 1.88 ppm (q, CH$_2$—CH$_2$—COO—, one equivalent per mol of the product), 2.37 ppm (t, —CH$_2$—COO—, one equivalent per mol of the product), 2.69 ppm (s, free N-hydroxysuccinimide peak), 2.82 ppm (s, —O—(C=O)O—NHS, three equivalents per mol of the product), 3.33 ppm (s, —C—CH$_2$—O—), 3.63 ppm (bm, —C—CH$_2$—O—, —OCH$_3$, and PEG backbone), 3.77 ppm (m, —CH$_2$CH$_2$O-succinimidyl carbonate, three equivalents per mol of the product), 4.44 ppm (m, —CH$_2$CH$_2$O-succinimidyl carbonate, three equivalents per mol of the product).

D. 3ARM-PEG3 (15 KDa)-butanoic acid

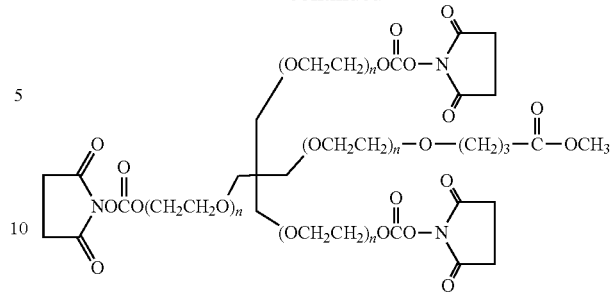

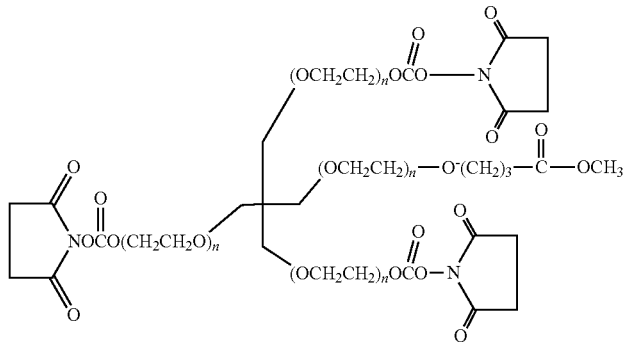

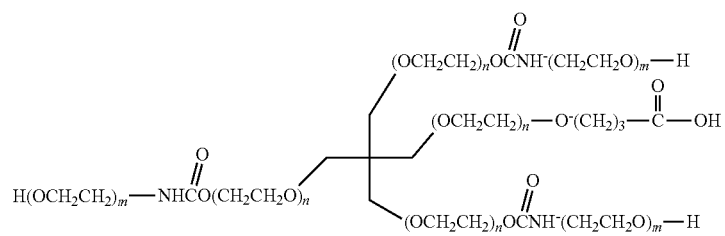

A solution of HO-PEG (5 KDa)-Amine (Nektar Therapeutics, 2.0 g, 0.00040 moles) in toluene (20 ml) was azeotropically dried by distilling off toluene under reduced pressure. The dried product was dissolved in anhydrous acetonitrile (20 ml) and triethylamine (0.15 ml) was added. Next pentaerythritol ethoxylate-mono-butanoic acid, methyl ester, tri-succinimidyl carbonate solution (1.07 g, 0.000358 succinimidyl carbonate equivalents) was added and the mixture was stirred overnight at room temperature under argon atmosphere. The solvent was distilled off under reduced pressure. The product was dissolved in 30 ml deionized water and the pH of the solution was adjusted to 12.1 by addition of 5% aqueous NaOH. The solution was stirred for 2 hours at pH 12.0+/−0.1. Next NaCl (3 g) was added and the pH was adjusted to 3.0 with 5% $H_3PO_4$. The product was extracted with dichloromethane (3×30 ml). The extract was dried with anhydrous $MgSO_4$ and the solvent was distilled off under reduced pressure giving 1.7 g of white solid product.

HPLC analysis showed that the product was about 85% pure and was contaminated with high molecular weight (5.4 wt %) and low molecular weight (10.2 wt %) impurities. The product was purified by ion exchange chromatography using DEAE Sepharose FF media giving 0.75 g of 100% pure (meaning it is believed that the product comprised a single polymer specie) mPEG3 (15 KDa)-butanoic acid. Gel permeation chromatography showed that molecular weight of the product was 14,168 Da.

Example 2

4ARM-PEG (20 KDa)-mono-butanoic acid

A. Pentaerythritol ethoxylate-mono-PEG (5 KDa)-butanoic acid, methyl ester

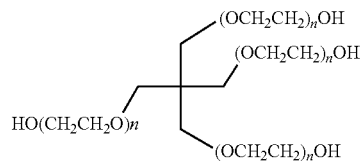

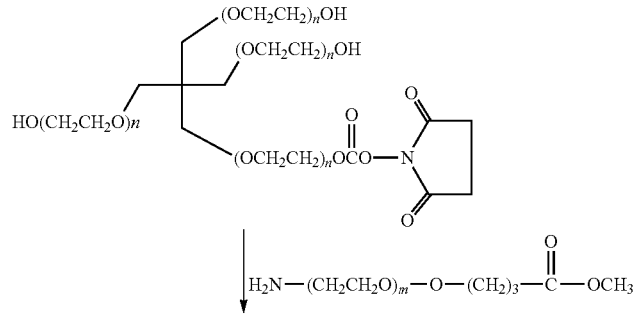

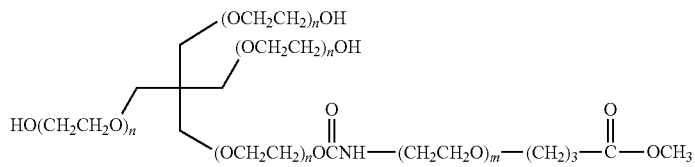

Where n is independently equal 0 to 8

A solution of pentaerythritol ethoxylate (3/4 EO/OH) (25 g, 0.370 OH equivalents), in toluene (100 ml) was azeotropically dried by distilling off toluene under reduced pressure. The dried pentaerythritol ethoxylate was dissolved in anhydrous acetonitrile (100 ml) and anhydrous pyridine (4.2 ml) and di-succinimidyl carbonate (9.5 g, 0.037 moles) were added and the mixture was stirred overnight at room temperature under argon atmosphere. Next PEG (5 KDa)-α-amine-ω-butanoic acid, methyl ester (20 g, 0.0040 moles) and triethylamine were added and the reaction mixture was stirred overnight at room temperature under argon atmosphere. The solvent was distilled off under reduced pressure. The crude product was dissolved in dichloromethane (20 ml) and isopropyl alcohol (700 ml) was added at room temperature. The precipitated product was filtered off and dried under vacuum giving 19 g of white solid.

NMR ($d_6$-DMSO): 1.71 ppm (q, C$\underline{H_2}$—CH$_2$—COO—) 2.24 ppm (t, —CH$_2$—COO—), 3.25 ppm (s, —C—CH$_2$—O—), 3.51 ppm (s, PEG backbone).

GPC analysis showed that product contained 95.7% of the desired product having a molecular weight ~5 KDa and 4.3% of dimer having a molecular weight ~10 KDa.

B. Pentaerythritol ethoxylate-mono-PEG (5 KDa)-butanoic acid, methyl ester, tri-succinimidyl carbonate Pentaerythritol ethoxylate-mono-PEG (5 KDa)-butanoic acid, methyl ester (5.0 g. 0.0030 —OH equivalents) was dissolved in anhydrous toluene (100 ml). Next toluene was distilled off under reduced pressure. The dried product was dissolved in anhydrous acetonitrile (25 ml) and anhydrous pyridine (0.34 ml) and disuccinimidyl carbonate (0.85 g, 0.0033 moles) were added to the solution. The mixture was stirred overnight at room temperature under argon atmosphere. NMR analysis showed that all hydroxyl groups were converted to succinimidyl carbonate esters and the mixture also contained residual disuccinimidyl carbonate (0.000317 moles). Water (0.005 ml) was added and the mixture was stirred overnight at room temperature under an argon atmosphere. Consecutive NMR analysis showed that product was still 100% substituted but residual disuccinimidyl carbonate was completely hydrolyzed. The resulting solution was used directly in the next synthetic step.

NMR (CDCl$_3$): 1.88 ppm (q, C$\underline{H_2}$—CH$_2$—COO—, one equivalent per mol of the product), 2.37 ppm (t, —CH$_2$—COO—, one equivalent per mol of the product), 2.69 ppm (s, free N-hydroxysuccinimide peak), 2.82 ppm (s, —O—(C=O)O—NHS, three equivalents per mol of the product), 3.33 ppm (s, —C—CH$_2$—O—), 3.63 ppm (bm, —C—CH$_2$—O—, —OCH$_3$, and PEG backbone), 3.77 ppm (m, —C$\underline{H_2}$CH$_2$O-succinimidyl carbonate, three equivalents per mol of the product), 4.44 ppm (m, —CH$_2$CHO-succinimidyl carbonate, three equivalents per mol of the product).

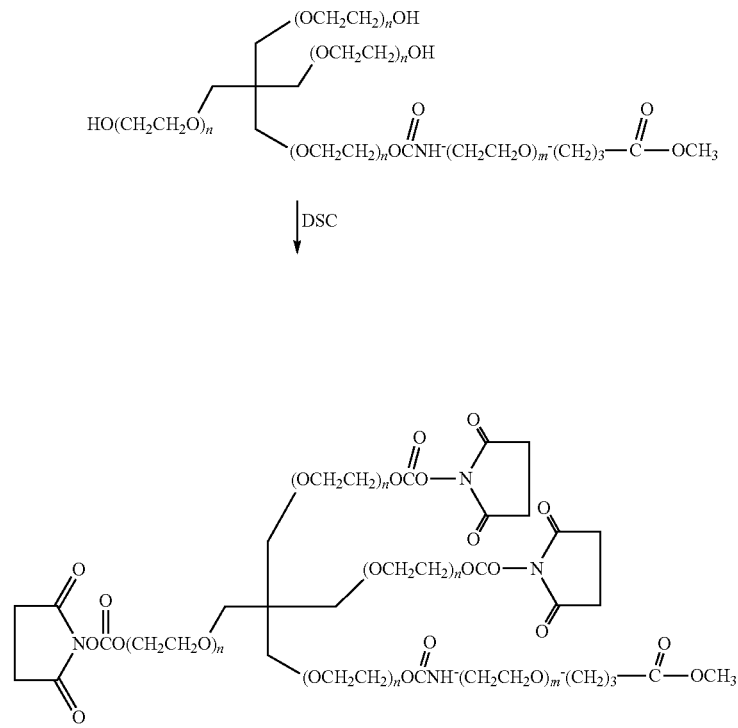

C. 4ARM-PEG (20 KDa)-mono-butanoic acid

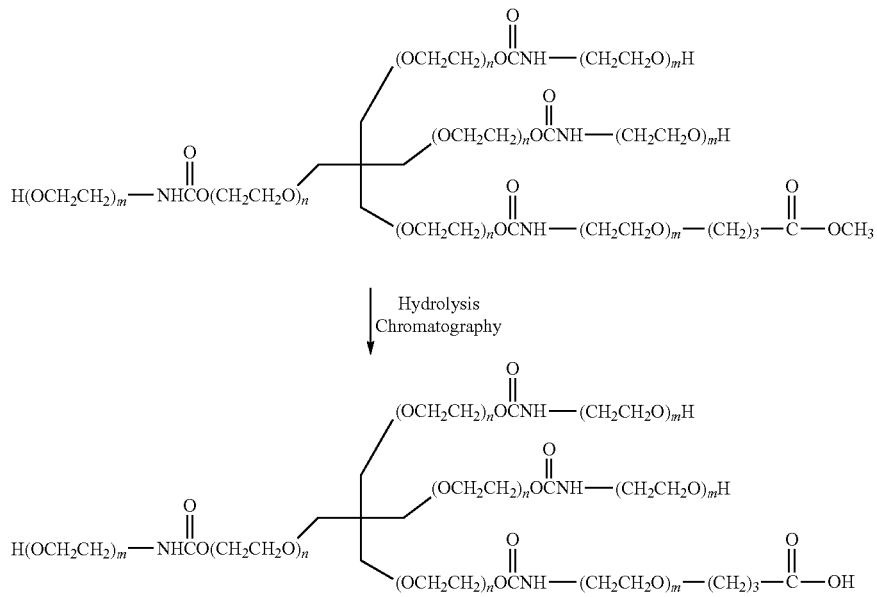

A solution of PEG (5 KDa)-α-hydroxy-ω-amine (Nektar Therapeutics, 16.5 g, 0.00330 moles) in toluene (165 ml) was azeotropically dried by distilling off toluene under reduced pressure. The dried product was dissolved in anhydrous acetonitrile (200 ml) and triethylamine (1.25 ml) was added. Next the solution of pentaerythritol ethoxylate-mono-PEG (5 KDa)-butanoic acid, methyl ester, tri-succinimidyl carbonate containing 5.0 g of the solid compound (0.00300 succinimidyl carbonate equivalents) was added and the mixture was stirred overnight at room temperature under argon atmosphere. The solvent was distilled off under reduced pressure. The product was dissolved in 220 ml deionized water and the pH of the solution was adjusted to 12.1 by addition of 5% aqueous NaOH. The solution was stirred 2 hours at the pH 12.0+/−0.1. Next NaCl (20 g) was added and the pH was adjusted to 3.0 with 5% $H_3PO_4$. The product was extracted with dichloromethane (250, 150, and 100 ml). The extract was dried with anhydrous $MgSO_4$ and the solvent was distilled off under reduced pressure giving 19.5 g of white solid product.

HPLC analysis showed that the product was 58.6% pure and was contaminated with high molecular weight (19.4 wt %) and low molecular weight (22.0 wt %) impurities.

The product was purified by ion exchange chromatography using DEAE Sepharose FF media giving 7.3 g of 100% pure 4ARM-PEG (20 KDa)-mono-butanoic acid. Gel permeation chromatography showed that molecular weight of the product was 19,461 Da.

The invention set forth herein has been described with respect to particular exemplified embodiments. However, the foregoing description is not intended to limit the invention to the exemplified embodiments, and the skilled artisan should recognize that variations can be made within the spirit and scope of the invention as described in the foregoing specification. On the contrary, the invention includes all alternatives, modifications, and equivalents that may be included within the true spirit and scope of the invention.

We claim:

1. A chromatographically purified branched polyol having the structure Y—R(—OH)$_p$, wherein R is a branched hydrocarbon, Y is an ionizable functional group selected from the group consisting of amine and carboxylic acid, and p is at least 2, and further wherein (i) the branched polyol has a single ionizable functional group, optionally in protected form, (ii) the polyol has a purity of at least about 83%, and (iii) the R group includes a poly(alkylene glycol) chain of 1 to about 25 monomer subunits attached to each terminal hydroxyl group.

2. The branched polyol of claim 1, wherein the polyol has a purity of at least about 91%.

3. The branched polyol of claim 2, wherein the polyol has a purity of at least about 97%.

4. The branched polyol of claim 3, wherein the polyol has a purity of about 100%.

5. The branched polyol of claim 1, wherein p is 3 to about 25.

6. The branched polyol of claim 1, wherein p is 3 to about 10.

* * * * *